United States Patent
Buysman et al.

(10) Patent No.: US 11,272,981 B2
(45) Date of Patent: Mar. 15, 2022

(54) ELECTRODE ASSEMBLY FOR CATHETER SYSTEM

(71) Applicant: St. Jude Medical, Cardiology Division, Inc., St. Paul, MN (US)

(72) Inventors: John Jason Buysman, Minnetonka, MN (US); Gregory James Dakin, Edina, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 551 days.

(21) Appl. No.: 16/018,733

(22) Filed: Jun. 26, 2018

(65) Prior Publication Data
US 2018/0303546 A1 Oct. 25, 2018

Related U.S. Application Data

(62) Division of application No. 14/258,398, filed on Apr. 22, 2014, now abandoned.
(Continued)

(51) Int. Cl.
*A61B 18/14* (2006.01)
*A61B 18/00* (2006.01)

(52) U.S. Cl.
CPC ............ *A61B 18/1492* (2013.01); *A61B 2018/00267* (2013.01)

(58) Field of Classification Search
CPC ........ A61B 18/1492; A61B 2018/0016; A61B 2018/00214; A61B 2018/00267;
(Continued)

(56) References Cited

U.S. PATENT DOCUMENTS

| 3,650,277 A | 3/1972 | Sjostrand et al. |
| 4,658,819 A | 4/1987 | Harris et al. |

(Continued)

FOREIGN PATENT DOCUMENTS

| WO | 9745157 A1 | 12/1997 |
| WO | 0066020 A1 | 11/2000 |

(Continued)

OTHER PUBLICATIONS

Abboud, Francois M., The Sympathetic System in Hypertension, State-of-the-Art Review, Hypertension Journal of the American Heart Association, Hypertension 4 (suppl II): 11-208-11-225, 1982.
(Continued)

*Primary Examiner* — Thomas A Giuliani
(74) *Attorney, Agent, or Firm* — Armstrong Teasdale LLP

(57) ABSTRACT

In an electrode assembly for a catheter system, a plurality of struts extends from a proximal end to a distal end of the electrode assembly. Each strut has a longitudinally extending proximal leg, a longitudinally extending distal leg, and a center segment extending between and interconnecting the proximal leg and the distal leg. A hinge interconnects the proximal leg and the center segment, and another hinge interconnects the distal leg and the center segment. The center segment of each of the struts has a corresponding electrode thereon. The electrode assembly is configurable between a collapsed configuration and an expanded configuration, with the electrodes being transversely spaced from the longitudinal axis of the electrode assembly a greater distance in the expanded configuration than in the collapsed configuration.

15 Claims, 23 Drawing Sheets

Related U.S. Application Data

(60) Provisional application No. 61/842,646, filed on Jul. 3, 2013.

(58) Field of Classification Search
CPC .......... A61B 2018/00279; A61B 2018/00404; A61B 2018/00577; A61B 2018/1465
USPC .................................................. 606/41, 49
See application file for complete search history.

(56) References Cited

U.S. PATENT DOCUMENTS

| | | | |
|---|---|---|---|
| 5,035,694 A | 7/1991 | Kasprzyk et al. |
| 5,255,679 A | 10/1993 | Imran |
| 5,300,068 A | 4/1994 | Rosar et al. |
| 5,368,591 A | 11/1994 | Lennox et al. |
| 5,387,233 A | 2/1995 | Alferness et al. |
| 5,465,717 A | 11/1995 | Imran et al. |
| 5,531,779 A | 7/1996 | Dahl et al. |
| 5,598,848 A | 2/1997 | Swanson et al. |
| 5,607,462 A | 3/1997 | Imran |
| 5,628,313 A | 5/1997 | Webster, Jr. |
| 5,676,662 A | 10/1997 | Fleischhacker et al. |
| 5,707,400 A | 1/1998 | Terry, Jr. et al. |
| 5,769,077 A | 6/1998 | Lindegren |
| 5,772,590 A | 6/1998 | Webster, Jr. |
| 5,893,885 A | 4/1999 | Webster, Jr. |
| 5,897,553 A | 4/1999 | Mulier et al. |
| 5,954,649 A | 9/1999 | Chia et al. |
| 5,954,719 A | 9/1999 | Chen et al. |
| 6,004,269 A | 12/1999 | Crowley et al. |
| 6,012,457 A | 1/2000 | Lesh |
| 6,014,589 A * | 1/2000 | Farley ................ A61B 18/1492 606/191 |
| 6,016,437 A | 1/2000 | Tu et al. |
| 6,024,740 A | 2/2000 | Lesh et al. |
| 6,073,048 A | 6/2000 | Kieval et al. |
| 6,096,037 A | 8/2000 | Mulier et al. |
| 6,117,101 A | 9/2000 | Diederich et al. |
| 6,161,543 A | 12/2000 | Cox et al. |
| 6,178,349 B1 | 1/2001 | Kieval |
| 6,200,312 B1 | 3/2001 | Zikorus et al. |
| 6,216,044 B1 | 4/2001 | Kordis |
| 6,233,491 B1 | 5/2001 | Kordis et al. |
| 6,283,951 B1 | 9/2001 | Flaherty et al. |
| 6,287,608 B1 | 9/2001 | Levin et al. |
| 6,292,695 B1 | 9/2001 | Webster, Jr. et al. |
| 6,322,559 B1 | 11/2001 | Daulton et al. |
| 6,460,545 B2 | 10/2002 | Kordis |
| 6,488,673 B1 | 12/2002 | Laufer et al. |
| 6,522,926 B1 | 2/2003 | Kieval et al. |
| 6,613,045 B1 | 9/2003 | Laufer et al. |
| 6,616,624 B1 | 9/2003 | Kieval |
| 6,635,054 B2 | 10/2003 | Fjield et al. |
| 6,656,174 B1 | 12/2003 | Hegde et al. |
| 6,669,655 B1 | 12/2003 | Acker et al. |
| 6,699,231 B1 | 3/2004 | Sterman et al. |
| 6,748,255 B2 | 6/2004 | Fuimaono et al. |
| 6,805,131 B2 | 10/2004 | Kordis |
| 6,845,267 B2 | 1/2005 | Harrison et al. |
| 6,954,977 B2 | 10/2005 | Maguire et al. |
| 6,970,730 B2 | 11/2005 | Fuimaono et al. |
| 7,122,031 B2 | 10/2006 | Edwards et al. |
| 7,149,574 B2 | 12/2006 | Yun et al. |
| 7,155,284 B1 | 12/2006 | Whitehurst et al. |
| 7,162,303 B2 | 1/2007 | Levin et al. |
| 7,245,955 B2 | 7/2007 | Rashidi |
| 7,291,146 B2 | 11/2007 | Steinke et al. |
| 7,363,076 B2 | 4/2008 | Yun et al. |
| 7,419,486 B2 | 9/2008 | Kampa |
| 7,465,288 B2 | 12/2008 | Dudney et al. |
| 7,468,062 B2 | 12/2008 | Oral et al. |
| 7,481,803 B2 | 1/2009 | Kesten et al. |
| 7,653,438 B2 | 1/2010 | Deem et al. |
| 7,717,948 B2 | 5/2010 | Demarais et al. |
| 7,742,795 B2 | 6/2010 | Stone et al. |
| 7,850,685 B2 | 12/2010 | Kunis et al. |
| 7,949,407 B2 | 5/2011 | Kaplan et al. |
| 8,145,316 B2 | 3/2012 | Deem et al. |
| 8,224,416 B2 | 7/2012 | De La Rama et al. |
| 8,256,428 B2 | 9/2012 | Hindricks et al. |
| 8,343,213 B2 | 1/2013 | Salahieh et al. |
| 8,347,891 B2 | 1/2013 | Demarais et al. |
| 8,442,639 B2 | 5/2013 | Walker et al. |
| 8,454,594 B2 | 6/2013 | Demarais et al. |
| 8,545,495 B2 | 10/2013 | Scheib |
| 9,022,948 B2 | 5/2015 | Wang |
| 2002/0068885 A1 | 6/2002 | Harhen et al. |
| 2002/0120304 A1 | 8/2002 | Mest |
| 2003/0009208 A1 | 1/2003 | Snyder et al. |
| 2003/0050681 A1 | 3/2003 | Pianca et al. |
| 2003/0060858 A1 | 3/2003 | Kieval et al. |
| 2003/0074039 A1 | 4/2003 | Puskas |
| 2003/0114739 A1 | 6/2003 | Fuimaono et al. |
| 2003/0216792 A1 | 11/2003 | Levin et al. |
| 2003/0233099 A1 | 12/2003 | Danaek et al. |
| 2004/0215186 A1 | 10/2004 | Cornelius et al. |
| 2005/0288730 A1 | 12/2005 | Deem et al. |
| 2006/0089678 A1 | 4/2006 | Shalev |
| 2007/0135875 A1 | 6/2007 | Demarais et al. |
| 2008/0255478 A1 | 10/2008 | Burdette |
| 2008/0262489 A1 | 10/2008 | Steinke |
| 2009/0076409 A1 | 3/2009 | Wu et al. |
| 2010/0016762 A1 | 1/2010 | Thapliyal et al. |
| 2010/0094209 A1 | 4/2010 | Drasler et al. |
| 2010/0168737 A1 | 7/2010 | Grunewald |
| 2010/0249773 A1 | 9/2010 | Clark et al. |
| 2010/0268307 A1 | 10/2010 | Demarais et al. |
| 2010/0286684 A1 | 11/2010 | Hata et al. |
| 2011/0004087 A1 | 1/2011 | Fish et al. |
| 2011/0118726 A1* | 5/2011 | De La Rama ..... A61B 18/1492 606/33 |
| 2011/0137298 A1 | 6/2011 | Nguyen et al. |
| 2011/0160720 A1 | 6/2011 | Johnson et al. |
| 2011/0213231 A1 | 9/2011 | Hall et al. |
| 2011/0257641 A1 | 10/2011 | Hastings et al. |
| 2011/0264011 A1 | 10/2011 | Wu et al. |
| 2011/0264086 A1 | 10/2011 | Ingle |
| 2012/0143097 A1 | 6/2012 | Pike, Jr. |
| 2012/0143298 A1 | 6/2012 | Just et al. |
| 2012/0296232 A1* | 11/2012 | Ng ........................... A61B 5/24 600/554 |
| 2012/0323233 A1 | 12/2012 | Maguire et al. |
| 2013/0116737 A1 | 5/2013 | Edwards et al. |
| 2013/0131743 A1 | 5/2013 | Yamasaki et al. |
| 2013/0144251 A1 | 6/2013 | Sobotka |
| 2013/0172715 A1 | 7/2013 | Just et al. |
| 2014/0128949 A1* | 5/2014 | Hollett ................. A61N 1/0519 607/116 |
| 2014/0324043 A1* | 10/2014 | Terwey .............. A61B 18/1492 606/41 |
| 2015/0270634 A1 | 9/2015 | Buesseler et al. |

FOREIGN PATENT DOCUMENTS

| | | | |
|---|---|---|---|
| WO | 0100273 A1 | 1/2001 |
| WO | 0122897 A1 | 4/2001 |
| WO | 0226314 A1 | 4/2002 |
| WO | 03082080 A2 | 10/2003 |
| WO | 2006041881 A2 | 4/2006 |
| WO | 2007149970 A2 | 12/2007 |
| WO | 2008141150 A2 | 11/2008 |
| WO | 2008151001 A2 | 12/2008 |
| WO | 2012064818 A1 | 5/2012 |
| WO | 2012106492 A1 | 8/2012 |

OTHER PUBLICATIONS

Allen, Edgar V., Sympathectomy for Essential Hypertension, Circulation Journal of the American Heart Association, vol. VI, Jul. 1952, 131-140.

(56) References Cited

OTHER PUBLICATIONS

Anderson, Erling A. et al, Elevated Sympathetic Nerve Activity in Borderline Hypertensive Humans, Evidence From Direct Intraneural Recordings, Hypertension Journal of the American Heart Association, vol. 14, No. 2, Aug. 1989, 177-183.

Ardian, Inc., Ardian(R) Receives 2010 EuroPCR Innovation Award and Demonstrates Further Durability of Renal Denervation Treatment for Hypertension, PR Newswire, Jun. 3, 2010.

Arentz, Thomas et al, Feasibility and Safety of Pulmonary Vein Isolation Using a New Mapping and Navigation System in Patients with Refractory Atrial Fibrillation, Circulation Journal of the American Heart Association, Nov. 18, 2003, 2484-2490.

Badoer, Emilio et al, Cardiac Afferents Play the Dominant Role in Renal Nerve Inhibition Elicited by Volume Expansion in the Rabbit, American Journal of Physiology, 1998, R383-R388.

Bakris, George L. et al, Baroreflex Activation Therapy Provides Durable Benefit in Patients with Resistant Hypertension: Results of Long-Term Follow-up in the Rheas Pivotal Trial, J Am Soc Hypertens. Mar.-Apr. 2012;6(2):152-8.

Bao, Gang et al, Blood Pressure Response to Chronic Episodic Hypoxia: Role of the Sympathetic Nervous System, American Journal of Physiology, 1997, 95-101.

Barajas, Luciano et al, Anatomy of the Renal Innervation: Intrarenal Aspects and Ganglia of Origin, Canadian Journal of Physiology and Pharmacology, vol. 70, No. 5, May 1992, 735-749.

Barajas, Luciano et al, Monoaminergic Innervation of the Rat Kidney: A Quantitative Study, American Journal of Physiology, vol. 259, No. 3, Sep. 1990, F503-F511.

Bardram, Linda et al, Late Results After Surgical Treatment of Renovascular Hypertension, A Follow-up Study of 122 Patients 2-18 Years After Surgery, Annals of Surgery, vol. 201, No. 2, Feb. 1985, 219-224.

Bello-Reuss, Elsa et al, Effect of Renal Sympathetic Nerve Stimulation on Proximal Water and Sodium Reabsorption, The Journal of Clinical Investigation, vol. 57, Apr. 1976, 1104-1107.

Bello-Reuss, Elsa et al, Effects of Acute Unilateral Renal Denervation in the Rat, The Journal of Clinical Investigation, vol. 56, Jul. 1975, 208-217.

Benito, Fernando et al, Radiofrequency Catheter Ablation of Accessory Pathways in Infants, Heart, 1997, 78, 160-162.

Bernardi, Luciano et al, Influence of Type of Surgery on the Occurrence of Parasympathetic Reinnervation After Cardiac Transplantation, Circulation Journal of the American Heart Association, Apr. 14, 1998;97(14):1368-74.

Bertog, Stefan C. et al, Renal Denervation for Hypertension, JACC: Cardiovascular Interventions, vol. 5, No. 3, Mar. 2012, 249-258.

Bertram, Harald et al, Coronary Artery Stenosis After Radiofrequency Catheter Ablation of Accessory Atrioventricular Pathways in Children with Ebstein's Malformation, Circulation Journal of the American Heart Association, 2001, 538-543.

Blankestijn, Peter J. et al, Renal Denervation: Potential Impacton Hypertension in Kidney Disease?, Nephrol Dial Transplant (2011) O: 1-3.

Blankestijn, Peter J. et al, Sympathetic Overactivity in Renal Failure Controlled by ACE Inhibition: Clinical Significance, Nephrol Dial Transplant, 2000, 15, 755-758.

Blum, Ulrich et al, Treatment of Ostial Renal-Artery Stenoses with Vascular Endoprostheses After Unsuccessful Balloon Angioplasty, The New England Journal of Medicine, vol. 336, No. 7, Feb. 1997, 459-465.

Brinkmann, Julia et al, Catheter-Based Renal Nerve Ablation and Centrally Generated Sympathetic Activity in Difficult-to-Control Hypertensive Patients Prospective Case Series, Hypertension. 2012;60: 1485-1490.

Brookes, Linda et al, Renal Denervation: Is Reality Meeting Expectations?, An Interview with Michel Azizi, MD, PhD, Medscape, Jan. 7, 2013.

Bunte, Matthew C. et al, Endovascular Treatment of Resistant and Uncontrolled Hypertension, JACC: Cardiovascular Interventions, vol. 6, No. 1, 2013, 1-9.

Calleary, Hickey D. et al, Pre-Transplant Bilateral Native Nephrectomy for Medically Refractory Hypertension, The Irish Medical Journal, Jul.-Aug. 2001;94(7):214-6.

Callens, David J. et al, Narrowing of the Superior Vena Cava-Right Atrium Junction During Radiofrequency Catheter Ablation for Inappropriate Sinus Tachycardia: Analysis with Intracardiac Echocardiography, Journal of the American College of Cardiology, vol. 33, No. 6, 1999, 1667-1670.

Campese, V.M., Is Hypertension in Chronic Renal Failure Neurogenic in Nature?, Nephrol Dial Transplant, 1994, 9: 741-742.

Campese, Vito M. et al, Neurogenic Factors in Renal Hypertension, Current Hypertension Reports, 2002 4: 256-260.

Campese, Vito M. et al, Renal Afferent Denervation Prevents Hypertension in Rats With Chronic Renal Failure, Hypertension, 1995, 25, 878-882.

Campese, Vito M. et al, Renal Afferent Denervation Prevents the Progression of Renal Disease in the Renal Ablation Model of Chronic Renal Failure in Rat, American Journal of Kidney Disease, vol. 26, No. 5, Nov. 1995, 861-865.

Campese, Vito M., Interventional Hypertension: A New Hope or a New Hype? The Need to Redefine Resistant Hypertension, J Hypertens. Nov. 2013;31(11):2118-21.

Canadian Agency for Drugs and Technologies in Health, Catheter-Based Renal Denervation for Treatment-Resistant Hypertension; Issues in Emerging Health Technologies, Issue 121, Mar. 2013.

Carlstedt, Thomas et al, Regrow1h of Lesioned Dorsal Root Nerve Fibers into the Spinal Cord of Neonatal Rats, Neuroscience Letters Feb. 10, 1987;74(1):14-8.

Chabanier, H. et al, On the Decapsulation and Neurectomy of the Kidnesy in Permanent Hypertensive States, The Medical Press, Feb. 22, 1936, No. 16, 307-310.

Ciccone, C D et al, Effects of Acute Renal Denervation on Kidney Function in Deoxycorticosterone Acetate-Hypertensive Swine, Hypertension Journal of the American Heart Association, Oct. 1986, vol. 8, No. 10, 925-931.

Ciriello, John et al, Renal Afferents and Hypertension, Current Hypertension Reports 2002, 4:136-142.

Converse, Richard L. et al, Sympathetic Overactivity in Patients with Chronic Renal Failure, The New England Journal of Medicine, vol. 327, No. 27, 1992, 1912-1918.

Crile, George, The Clinical Results of Celiac Ganglionectomy in the Treatment of Essential Hypertension, Annals of Surgery, Jun. 1938; 107(6): 909-916.

Cruickshank, J.M., Beta-Blockers Continue to Surprise Us, European Heart Journal (2000) 21, 354-364.

Curtis, John J. et al, Surgical Therapy for Persistent Hypertension After Renal Transplantation, Transplantation, vol. 31, No. 2, 1981, 125-128.

Dailey, U.G., Surgical Treatment of Hypertension: A Review-Part 11, Journal of the National Medical Association, May 1948, vol. 40, No. 3., 113-116.

Dailey, U.G., Surgical Treatment of Hypertension: A Review-Part 111, Journal of the National Medical Association, Jul. 1948, vol. 40, No. 4, 160-162.

Dailey, U.G., The Surgical Treatment of Hypertension: A Review, Journal of the National Medical Association, Mar. 1948, vol. 40, No. 2, 76-79.

Davis, Mark I. et al, Effectiveness of Renal Denervation Therapy for Resistant Hypertension a Systematic Review and Meta-Analysis, Journal of the American College of Cardiology, vol. 62, No. 3, 2013, 231-241.

De Wardener, H.E., The Hypothalamus and Hypertension, Physiological Reviews,vol. 81, No. 4, Oct. 2001.

Dequattro V. et al, The Sympathetic Nervous System: The Muse of Primary Hypertension, Journal of Human Hypertension, 2002, 16 (Suppl 1), S64-S69.

Dibona, Gerald F. et al, Neural Control of Renal Function, Physiological Reviews, vol. 77, No. 1, Jan. 1997, 75-197.

Dibona, Gerald F. et al, Translational Medicine: The Antihypertensive Effect of Renal Denervation, America! Journal of Physiology, 2010, 298, R245-R253.

(56) References Cited

OTHER PUBLICATIONS

Dibona, Gerald F., Neural Control of Renal Function: Cardiovascular Implications, Hypertension Journal of the American Heart Association, vol. 13, No. 6, Part 1, Jun. 1989, 539-548.
Dibona, Gerald F., Neural Control of the Kidney: Functionally Specific Renal Sympathetic Nerve Fibers, American Journal of Physiology, 2000, 279, R1517-R1524.
Dibona, Gerald F., Neural Control of the Kidney: Past, Present, and Future, Hypertension Journal of the American Heart Association, vol. 41, Mar. 2003, Part 11, 621-624.
Robbins, Ivan M. et al, Pulmonary Vein Stenosis After Catheter Ablation of Atrial Fibrillation, Circulation Journal of the American Heart Association, 1998;98:1769-1775.
Rocha-Singh, Krishna J., Catheter-Based Sympathetic Renal Denervation a Novel Strategy for the Treatment of Resistant Hypertension, Endovascular Today, Aug. 2009, 52-56.
Rocha-Singh, Krishna J., Renal Artery Denervation: A Brave New Frontier, Endovascular Today, Feb. 2012, 45-53.
Sanderson, John E. et al, Effect of B-Blockade on Baroreceptor and Autonomic Function in Heart Failure, Clinical Science (1999) 96, 137-146.
Santos, Mario et al, Renal Sympathetic Denervation in Resistant Hypertension, World J Cardiol Apr. 26, 2013; 5(4):94-101.
Savard, Sebastien et al, Eligibility for Renal Denervation in Patients With Resistant Hypertension When Enthusiasm Meets Reality in Real-Life Patients, J Am Coll Cardiel. 2012;60(23):2422-2424.
Schauerte, Patrick et al, Catheter Ablation of Cardiac Autonomic Nerves for Prevention of Vagal Atrial Fibrillation, Circulation Journal of the American Heart Association, 2000, 102:2774-2780.
Schlaich, Markus P. et al, International Expert Consensus Statement: Percutaneous Transluminal Renal Denervation for the Treatment of Resistant Hypertension, Journal of the American College of Cardiology vol. 62, Issue 22, Dec. 3, 2013, pp. 2031-2045.
Schlaich, Markus P. et al, Renal Denervation as a Therapeutic Approach for Hypertension Novel Implications for an Old Concept, Hypertension Journal of the American Heart Association, 2009;54:1195-1201.
Schlaich, Markus P. et al, Renal Sympathetic-Nerve Ablation for Uncontrolled Hypertension, The New England Journal of Medicine, 2009; 361:932-934.
Schmieder, Roland E. et al, ESH Position Paper: Renal Denervation—An Iterventional Therapy of Resistant Hypertension, Journal of Hypertension, 2012, 30:837-841.
Schmieder, Roland E. et al, Updated EHS Position Paper on Interventional Therapy of Resistant Hypertension, EuroIntervention 2013; 9:R58-R66.
Sellers, Alfred M. et al, Adrenalectomy and Sympathectomy for Hypertension Ten Year Survival, Archives of Surgery, vol. 89, Nov. 1964, 880-886.
Sen, S.K., Some Observations on Decapsulation and Denervation of the Kidney, The British Journal of Urology, vol. 8, Issue 4, Dec. 1936, 319-328.
Shiraki, Iwao William, Correction of Renal Hypertension by Ligation of Stenotic Segmental Renal Artery, Urology, vol. IX, No. 3, Mar. 1977, 296-298.
Shonai, Takaharu et al, Renal Artery Aneurysm: Evaluation with Color Doppler Ultrasonography Before and After Percutaneous Transarterial Embolization, J Ultrasound Med 19:277-280, 2000.
Silver, Donald et al, Renovascular Hypertension From Renal Artery Compression by Congenital Bands, Annals of Surgery, Feb. 1976, 161-166.
Smith, Gardner W. et al, Surgical Results and the Diagnostic Evaluation of Renovascular Hypertension, Annals of Surgery, May 1968, 669-680.
Smith, Harold P. et al, Radiofrequency Neurolysis in a Clinical Model Neuropathological Correlation, J Neurosurg 55:246-253, 1981.
Smithwick, R.H., An Evaluation of the Surgical Treatment of Hypertension, The Bulletin, Nov. 1949; 25(11):698-716.
Smithwick, Reginald H. et al, Splanchnicectomy for Essential Hypertension, The Journal of the American Medical Association, vol. 152, No. 16, Aug. 1953, 1501-1504.
Solis-Herruzo, J.A. et al, Effects of Lumbar Sympathetic Block on Kidney Function in Cirrhotic Patients with Hepatorenal Syndrome, Journal of Hepatology, 1987; 5: 167-173.
Sowers, James R. et al, Diabetes, Hypertension, and Cardiovascular Disease: An Update, Hypertension Journal of the American Heart Association, 2001;37:1053-1059.
Stanley, James C, Surgical Treatment of Renovascular Hypertension, The American Journal of Surgery, vol. 174, Aug. 1997, 102-110.
Stella, Andrea et al., Effects of Reversible Renal Denervation on Haemodynamic and Excretory Functions of the Ipsilateral and Contralateral Kidney in the Cat, Journal of Hypertension 1986, 4: 181-188.
Stuart, Candace, Newest Frontier in Cardiac Care: Kidneys; Cardiovascular Business, Dec. 13, 2012.
Stuart, Mary, Masterminds of Ardian: An Interview With Inventors Mark Gelfand and Howard Levin, Windhover Information, Start-Up Jan. 1, 2011.
Sun, Yingxian et al., Risk of Coronary Stenosis with Venous Ablation for Epicardial Accessory Pathways, PACE, Apr. 2001, Part 11, vol. 24, 605.
Swartz, John F. et al, Radiofrequency Endocardial Catheter Ablation of Accessory Atrioventricular Pathway Atrial Insertion Sites, Circulation Journal of the American Heart Association, 1993;87:487-499.
Teigen, Corey L. et al, Segmental Renal Artery Embolization for Treatment of Pediatric Renovascular Hypertension, Journal of Vascular and Interventional Radiology, 1992; 3:111-117.
Teixeira, Maria Do Carmo et al,1992; Role of the Peripheral Renin Profile in Predicting Blood Pressure Control After Bilateral Nephrectomy in Renal-Transplanted Patients, Nephrol Dial Transplant (1998) 13: 2092-2097.
Teo, W S et al, Radiofrequency Catheter Ablation of Accessory Pathways: The Initial Experience in Singapore, Singapore Medical Journal, 1994; vol. 35:36-40.
Thiebot, J. et al, Bilateral Nephrectomy by Embolization of the Renal Arteries: A Report on Five Cases (author's transl), Sem Hop. Apr. 8-15, 1980;56(13-14):670-5.
Thomas, George et al, Renal Denervation to Treat Resistant Hypertension: Guarded Optimism, Cleveland Clinic Journal of Medicine, vol. 79, No. 7, Jul. 2012, 501-510.
Thomas, Natalie A., Secondary Consideration in Nonobviousness Analysis: The Use of Objective Indicia Following KSR V. Teleflex, NYU Law Review, vol. 86, No. 6, Dec. 2011, 2070-2112.
Ting, Chih-Tai et al, Arterial Hemodynamics in Human Hypertension Effects of Angiotensin Converting Enzyme Inhibition, Hypertension Journal of The American Heart Association, 1993;22:839-846.
Uchida, Fumiya et al, Effect of Radiofrequency Catheter Ablation on Parasympathetic Denervation: A Comparison of Three Different Ablation Sites, PACE, vol. 21, Nov. 1998, Part 11, 2517-2521.
Valente, John F. et al, Laparoscopic Renal Denervation for Intractable ADPKD-Related Pain, Nephrol Dial Transplant (2001) 16:160.
Villarreal, Daniel et al, Effects of Renal Denervation on Postprandial Sodium Excretion in Experimental Heart Failure, American Journal of Physiology, May 1994;266(5 Pt 2):R1599-R1604.
Von End, Oliver et al, Secondary Rise in Blood Pressure After Renal Denervation, The Lancet, vol. 380, Issue 9843, p. 778, Aug. 25, 2012.
Vujaskovic, Z. et al, Effects of Intraoperative Hyperthermia on Canine Sciatic Nerve: Histopathologic and Morphometric Studies, Int. J. Hyperthermia, 1994, vol. 10, No. 6, 845-855.
Webb, R.L. et al, Functional Identification of the Central Projections of Afferent Renal Nerves, Clin. and Exper.—Theory and Practice, Ag(SUPPL.I), 47-57 (1987).
Weinstock, Marta et al, Renal Denervation Prevents Sodium Retention and Hypertension in Salt-Sensitive Rabbits with Genetic Baroreflex Impairment, Clinical Science (1996) 90, 287-293.
Wilcox, Josiah N., Scientific Basis Behind Renal Denervation for the Control of Hypertension, Medtronic, Inc., Dec. 2012, 38 pages.

(56) References Cited

OTHER PUBLICATIONS

Winternitz, Sherry R. et al, Role of the Renal Sympathetic Nerves in the Development and Maintenance of Hypertension in the Spontaneously Hypertensive Rat, Journal of Clinical Investigation, vol. 66 Nov. 1980, 971-978.
Wolf-Maier, Katharina et al, Hypertension Treatment and Control in Five European Countries, Canada, and the United States, Hypertension. 2004;43:10-17.
Worthley, Stephen G. et al, Renal Denervation: How Do You Measure Success?, presentation 28 pages; Jul. 30, 2013.
Wyss, J.M. et al, Sensory Denervation of the Kidney Attenuates Renovascular Hypertension in the Rat, Am J Physiol Heart Circ Physiol 250:H82-H86, 1986.
Yamada, Yutaka et al, Age-Related Changes in Muscle Sympathetic Nerve Activity in Essential Hypertension, Hypertension Journal of the American Heart Association, 1989;13:870-877.
Young, Robert R. et al, Reversible Block of Nerve Conduction by Ultrasound Ultrasonic Blocking of Nerve Fibers, Arch Neural. 1961;4(1):83-89.
Moak, Jeffrey P. et al, Case Report: Pulmonary Vein Stenosis Following RF Ablation of Paroxysmal Atrial Fibrillation: Successful Treatment with Balloon Dilation, Journal of Interventional Cardiac Electrophysiology, Dec. 2000, 4, 4:621-631.
Mogil, Robert A. et al, Renal Innervation and Renin Activity in Salt Metabolism and Hypertension, American Journal of Physiology, vol. 216, No. 4, Apr. 1969, 693-697.
Morita, Hironobu et al, Neural Control of Urinary Sodium Excretion During Hypertonic NaC1 Load in Conscious Rabbits: Role of Renal and Hepatic Nerves and Baroreceptors, Journal of the Autonomic Nervous System, 34 (1991) 157-170.
Morrissey, D.M. et al, Sympathectomy in the Treatment of Hypertension, The Lancet, Feb. 1953, 403-408.
Mortara, Andrea et al, Nonselective Beta-Adrenergic Blocking Agent, Carvedilol, Improves Arterial Baroflex Gain and Heart Rate Variability in Patients With Stable Chronic Heart Failure, Journal of the American College of Cardiology, vol. 36, No. 5, 2000, 1612-1618.
Moss, Jonathan, Interventional Radiology and Renal Denervation, Interventions, vol. 13, Issue 3, 2013.
Naghavi, Morteza et al, Thermography Basket Catheter: In Vivo Measurement of the Temperature of Atherosclerotic Plaques for Detection of Vulnerable Plaques, Catheterization and Cardiovascular Interventions 59:52-59 (2003).
Naidoo, N. et al, Thoracic Splanchnic Nerves: Implications for Splanchnic Denervation, Journal of Anatomy, Nov. 2001;199(Pt 5):585-590.
Nakagawa, A. et al, Selective Ablation of Porcine and Rabbit Liver Tissue Using Radiofrequency: Preclinical Study, European Surgical Research, 1999;31:371-379.
Nakagawa, Hiroshi et al, Inverse Relationship Between Electrode Size and Lesion Size During Radiofrequency Ablation With Active Electrode Cooling, Circulation Aug. 4, 1998;98(5):458-465.
Nanni, Gregg S. et al, Control of Hypertension by Ethanol Renal Ablation, Radiology 148: 51-54, Jul. 1983.
Ndegwa, S., Catheter-Based Renal Denervation for Treatment-Resistant Hypertension [Issues in emerging health technologies issue 121]. Ottawa: Canadian Agency for Drugs and Technologies in Health; 2013.
Neutel, Joel M., Hypertension and Its Management: A Problem in Need of New Treatment Strategies, Journal of Renin-Angiotensin-Aldosterone System 2000 1: S10-S13.
Newcombe, C.P. et al, Sympathectomy for Hypertension, British Medical Journal, Jan. 1959, 142-144.
Ng, Fu Siong et al, Catheter Ablation of Atrial Fibrillation, Clinical Cardiology, 25, 384-394 (2002).
Norman, Roger A. et al, Role of the Renal Nerves in One-Kidney, One Clip Hypertension in Rats, Hypertension Journal of the American Heart Association, 1984;6:622-626.

Nozawa, Takashi et al, Effects of Long-Term Renal Sympathetic Denervation on Heart Failure After Myocardial Infarction in Rats, Heart Vessels (2002) 16:51-56.
O'Connor, Brian K. et al, Radiofrequency Ablation of a Posteroseptal Accessory Pathway via the Middle Cardiac Vein in a Six-Year-Old Child, PACE, vol. 20, Oct. 1997, Part 1, 2504-2507.
O'Hagen, Kathleen P. et al, Renal Denervation Decreases Blood Pressure in DOCA-Treated Miniature Swine With Established Hypertension, American Journal of Hypertension, 1990; 3:62-64.
Oliveira, Vera LL et al, Renal Denervation Normalizes Pressure and Baroreceptor Reflex in High Renin Hypertension in Conscious Rats, Hypertension vol. 19, No. 2 Feb. 1992, Supplement 11, 11-17-11-21.
Omran, Heyder et al, Echocardiographic Imaging of Coronary Sinus Diverticula and Middle Cardiac Veins in Patients with Preexcitation Syndrome: Impact—on Radiofrequency Catheter Ablation of Posteroseptal Accessory Pathways, PACE, vol. 18, Jun. 1995, 1236-1243.
Oparil, Suzanne et al, Renal Nerve Ablation: Emerging Role in Therapeutics; Blood Pressure, Oct. 2011, vol. 20, No. 5 , pp. 253-255.
Oral, Hakan et al, Pulmonary Vein Isolation for Paroxysmal and Persistent Atrial Fibrillation, Circulation Journal of the American Heart Association, 2002;105:1077-1081.
Osborn, Jeffrey L. et al, Long-Term Increases in Renal Sympathetic Nerve Activity and Hypertension, Clinical and Experimental Pharmacology and Physiology (1997) 24,72-76.
Osborn, John W., The Sympathetic Nervous System and Long-Term Regulation of Arterial Pressure: What Are the Critical Questions?, Clinical and Experimental Pharmacology and Physiology (1997) 24, 68-71.
Ou, Baiqing et al, Baroreflex Sensitivity Predicts the Induction of Ventricular Arrhythmias by Cesium Chloride in Rabbits, Japanese Circulation Journal, 1999; 63: 783-788.
Oz, Mehmet, Pressure Relief, TIME Magazine, Monday, Jan. 9, 2012.
Page, Irvine H. et al, Mechanisms, Diagnosis and Treatment of Hypertension of Renal Vascular Origin, Annal of Internal Medicine, Aug. 1959, vol. 51, No. 2, 196-211.
Page, Irvine H. et al, Mechanisms, Diagnosis and Treatment of Hypertension of Renal Vascular Origin; Annals of Internal Medicine, Aug. 1959;51:196-211.
Page, Irvine H. et al, The Effect of Renal Denervation on the Level of Arterial Blood Pressure and Renal Function in Essential Hypertension, Journal of Clinical Investigation, 1935;14(1):27-30.
Page, Irvine H. et al, The Effects of Renal Denervation on Patients Suffering from Nephritis, J Clin Invest. 1935;14(4):443-458.
Page, Irvine H., The Effect of Renal Efficiency of Lowering Arterial Blood Pressure in Cases of Essential Hypertension and Nephritis, Journal of Clinical Investigation, Nov. 1934; 13(6): 909-915.
Page, Max, Section of Surgery, Discussion on the Surgical Treatment of Hypertension, Proceedings of the Royal Society of Medicine, vol. XLI, Feb. 1948, 359-372.
Papademetriou, Vasilios, Hypertension and the Simplicity Renal Denervation System, Scientific Background, www.medtronic.com, 2011.
Pappone, Carlo et al, Circumferential Radiofrequency Ablation of Pulmonary Vein Ostia: A New Anatomic Approach for Curing Atrial Fibrillation, Circulation, Journal of The American Heart Association, 2000;102:2619-2628.
Parati, Gianfranco et al, The Human Sympathetic Nervous System: Its Relevance in Hypertension and Heart Failure, European Heart Journal (2012) 33, 1058-1066.
Parmar, Arundhati, Analyst: Medtronic Will Likely Acquire Another Hypertension Therapy Firm, Medcity News, Apr. 27, 2012; 3:06 p.m.; medcitynews.com.
Pavlovich, Christian P. et al, Percutaneous Radio Requency Ablation of Small Renal Tumors: Initial Results; The Journal of Urology, vol. 167, Jan. 10-15, 2002.
Pearce, John A. et al, Blood Vessel Architectural Features and Their Effect on Thermal Phenomena, Critical Reviews, vol. CR75, , Bellingham, WA: SPIE Optical Engineering Press; 2000, p. 231-277.

(56) References Cited

OTHER PUBLICATIONS

Peet, Max Minor, Hypertension and Its Surgical Treatment by Bilateral Supradiaphragmatic Splanchnicectomy, American Journal of Surgery, vol. 75, Issue 1, Jan. 1948, 48-68.
Perry, C. Bruce, Malignant Hypertension Cured by Unilateral Nephrectomy, British Heart Journal, Jul. 1945; 7(3):139-142.
Persu, Alexandre et al, Renal Denervation: Ultima Ratio or Standard in Treatment-Resistant Hypertension, Hypertension Journal of the American Heart Association, Sep. 2012;60(3):596-606.
Peterson, Helen Hogh et al, Lesion Dimensions During Temperature-Controlled Radiofrequency Catheter Ablation of Left Ventricular Porcine Myocardium Impact of Ablation Site, Electrode Size, and Convective Cooling, Circulation Journal of the American Heart Association, 1999;99:319-325.
Plouin, Pierre-Francois et al, Blood Pressure Outcome of Angioplasty in Atherosclerotic Renal Artery Stenosis a Randomized Trial, Hypertension Journal of the American Heart Association, 1998;31:823-829.
Poutasse, Eugene F., Surgical Treatment of Renal Hypertension, American Journal of Surgery, vol. 107, Jan. 1964, 97-103.
Pugsley, M.K. et al, The Vascular System an Overview of Structure and Function, Journal of Pharmacological and Toxicological Methods 44 (2000) 333-340.
Putney, John Paul, Are Secondary Considerations Still "Secondary"?: An Examination of Objective Indicia of Nonobviousness Five Years After KSR, Intellectual Property Brief, vol. 4, Issue 2, Article 5, 2012, 45-59.
Ramsay, Lawrence E. et al, Blood Pressure Response to Percutaneous Transluminal Angioplasty for Renovascular Hypertension: An Overview of Published Series; British Medical Journal Mar. 3, 1990; 300(6724): 569-572.
Rippy, Marian K. et al, Catheter-Based Renal Sympathetic Denervation: Chronic Preclinical Evidence for Renal Artery Safety, Clin Res Cardiel (2011) 100:1095-1101.
Ritz, Eberhard, New Approaches to Pathogenesis and Management of Hypertension, Clin J Am Soc Nephrol 4: 1886-1891, 2009.
Dibona, Gerald F., Renal Innervation and Denervation: Lessons from Renal Transplantation Reconsidered, Artificial Organs, vol. 11, No. 6, 1987, 457-462.
Dibona, Gerald F., Role of the Renal Nerves in Renal Sodium Retention and Edema Formation, Trans Am Clin Climatol Assoc. 1990; 101: 38-45.
Dibona, Gerald F., Sympathetic Nervous System and Hypertension, Hypertension Journal of the American Heart Association, 2013; 61: 556-560.
Dibona, Gerald F., Sympathetic Nervous System and the Kidney in Hypertension, Curr Opin Nephrol Hypertens. Mar. 2002;11(2):197-200.
Dibona, Gerald F., The Sympathetic Nervous System and Hypertension, Hypertension Journal of the American Heart Association, Vo. 43, Feb. 2004, 147-150.
Doumas, Michael et al, Interventional Management of Resistant Hypertension, The Lancet, vol. 373, Apr. 11, 2009, pp. 1228-1230.
Dubuc, Marc et al, Feasibility of Cardiac Cryoablation Using a Transvenous Steerable Electrode Catheter, Journal of Interventional Cardiac Electrophysiology, 1998, 2: 285-292.
Elmula, Fadl et al, Renal Sympathetic Denervation in Patients With Treatment-Resistant Hypertension After Witnessed Intake of Medication Before Qualifying Ambulatory Blood Pressure, Hypertension. 2013;62:526-532.
Esler, M. et al, Sympathetic Nerve Activity and Neurotransmitter Release in Humans: Translation from Pathophysiology into Clinical Practice, Scandinavian Physiological Society, 2003, 177, 275-284.
Esler, Murray D. et al, Renal Sympathetic Denervation in Patients with Treatment-Resistant Hypertension (The Symplicity HTN-2 Trial): A Randomised Controlled Trial, Lancet, 2010; 376:1903-1909.

Esler, Murray et al, Assessment of Human Sympathetic Nervous System Activity from Measurements of Norepinephrine Turnover, Hypertension Journal of the American Heart Association, vol. 11, No. 1, Jan. 1988, 3-20.
Evelyn, Kenneth A. et al, Effect of Thoracolumbar Sympathectomy on the Clinical Course of Primary (Essential) Hypertension, American Journal of Medicine, Feb. 1960, 188-221.
Freyberg, R. H. et al, The Effect on the Kidney of Bilateral Splanchnicectomy in Patients with Hypertension, The Journal of Clinical Investigation, vol. 16, Issue 1, Jan. 1937, 49-65.
Gafoor, Sameer et al, Nonresponders to Renal Denervation for Resistant Hypertension, Endovascular Today, Oct. 2013, 63-70.
Garel, L. et al, Fatal Outcome After Ethanol Renal Ablation in Child with End-Stage Kidneys; AJR 146:593-594, Mar. 1986.
Gazdar, A. F. et al, Neural Degeneration and Regeneration in Human Renal Transplants, The New England Journal of Medicine, vol. 238, No. 5, Jul. 1970, 222-224.
Goldberg, Michael R. et al, Reconstructive Vascular Surgery for Renovascular Hypertension, Can Med Assoc J. Feb. 2, 1974;110(3):275-80.
Golwyn, Daniel H. et al, Percutaneous Transcatheter Renal Ablation with Absolute Ethanol for Uncontrolled Hypertension or Nephrotic Syndrome: Results in 11 Patients with End-Stage Renal Disease, Journal of Vascular and Interventional Radiology, Jul.-Aug. 1997, vol. 8, No. 4, 527-533.
Gorisch, Wolfram et al, Heat-Induced Contraction of Blood Vessels, Lasers in Surgery and Medicine 2:1-13 (1982).
Grassi, Guido et al, Baroreflex Control of Sympathetic Nerve Activity in Essential and Secondary Hypertension, Hypertension Journal of the American Heart Association, 1998;31:68-72.
Grassi, Guido et al, Dissociation Between Muscle and Skin Sympathetic Nerve Activity in Essential Hypertension, Obesity, and Congestive Heart Failure, Hypertension. 1998;31:64-67.
Grimson, Keith S. et al, Results of Treatment of Patients with Hypertension by Total Thoracic and Partial to Total Lumbar Sympathectomy, Splanchnicectomy and Celiac Ganglionectomy, Annals of Surgery, Jun. 1949, vol. 129, No. 6, 850-871.
Grimson, Keith S. et al, Total Thoracic and Partial to Total Lumbar Sympathectomy, Splanchnicectomy and Celiac Ganglionectomy for Hypertension, Annals of Surgery, Oct. 1953, vol. 138, No. 4, 532-547.
Grimson, Keith S., Total Thoracic and Partial to Total Lumbar Sympathectomy and Celiac Ganglionectomy in the Treatment of Hypertension, Annals of Surgery, Oct. 1941, vol. 114, No. 4, 753-775.
Guyton, Arthur C., Blood Pressure Control Special Role of the Kidneys and Body Fluids, Science, vol. 252, Jun. 1991, 1813-1816.
Hafkenschiel, Joseph H. et al, Primary Hypertension Survey of the Survival of Patients with Established Diastolic Hypertension After Ten Years of Medical and Surgical Treatment, The American Journal of Cardiology, vol. 16, Jul. 1965, 61-66.
Hafkenschiel, Joseph H. et al, The Surgical Treatment of Hypertension with Particular Reference to Andrenalectomy and Sympathectomy, Transactions. American College of Cardiology, vol. 5, Dec. 1955, pp. 107-112.
Hall, J.E. et al, Role of Sympathetic Nervous System and Neuropeptides in Obesity Hypertension, Brazilian Journal of Medical and Biological Research, 2000, 33:605-618.
Hall, John E., The Kidney, Hypertension, and Obesity, Hypertension. 2003;41:625-633.
Hall, Winthrop H. et al, Combined Embolization and Percutaneous Radiofrequency Ablation of a Solid Renal Tumor, American Journal of Roentgenology, 174, Jun. 2000, 1592-1594.
Hamm, Christian et al, Confluence, Issue eight, Apr. 2014.
Han, Young-Min et al, Renal Artery Embolization with Diluted Hot Contrast Medium: An Experimental Study, Journal of Vascular and Interventional Radiology, Jul. 2001;12(7):862-868.
Hansen, Jesper Melchoir et al, The Transplanted Human Kidney Does Not Achieve Functional Reinnervation, Clinical Science, (1994) 87, 13-20.
Heuer, George J., The Surgical Treatment of Essential Hypertension, Annals of Surgery, Oct. 1936, vol. 104, No. 3, 771-786.

(56) References Cited

OTHER PUBLICATIONS

Hinton, J. William, End Results of Thoracolumbar Sympathectomy for Advanced Essential Hypertension, The Bulletin, Apr. 1948, 239-252.

Holmer, Stephan et al, Role of Renal Nerves for the Expression of Renin in Adult Rat Kidney, The American Journal of Physiology, May 1994;266(5 Pl 2):F738-F745.

Hoobler, S.W. et al, The Effects of Splanchnicectomy on the Blood Pressure in Hypertension, Circulation Journal of the American Heart Association, vol. IV, Aug. 1951, 173-183.

Hoppe, Uta C. et al, Minimally Invasive System for Baroreflex Activation Therapy Chronically Lowers Blood Pressure with Pacemaker-like Safety Profile: Results from the Barostim Neo Tlrial, J Am Soc Hypertens. Jul.-Aug. 2012;6(4):270-6.

Howard, James P. et al, Size of Blood Pressure Reduction from Renal Denervation: Insights from Meta-Analysis of Antihypertensive Drug Trials of 4121 Patients with Focus on Trial Design: the CONVERGE Report, Heart 2013;0:1-9.

Howard, James P. et al, Unintentional Overestimation of an Expected Antihypertensive Effect in Drug and Device Trials: Mechanisms and Solutions, International Journal of Cardiology, vol. 172, Issue 1, Mar. 1, 2014, pp. 29-35.

Howell, Marcus H. et al, Tandem Stenting of Crossed Renal Arteries with Ostial Stenosis, Tex Heart Inst J. 2000; 27(2): 166-169.

Hoye, Neil A. et al, Endovascular Renal Denervation: A Novel Sympatholylic with Relevance to Chronic Kidney Disease, Clinical Kidney Journal Advance Access, (2013) O: 1-8.

Huang, Shoei K. Stephen et al, Radiofrequency Catheter Ablation of Cardiac Arrhylhmias, Basic Concepts and Clinical Applications, Wiley-Blackwell, Jun. 2000, 1-12.

Huang, Wann-Chu, Renal Denervation Prevents and Reverses Hyperinsulinemia-Induced Hypertension in Rats, Hypertension Journal of the American Heart Association, 1998;32:249-254.

Humpreys, Michael H., Renal Nerves and CKD: Is Renal Denervation the Answer?, Journal of the American Socity of Nephrology, 2012, 23: 1-3.

International Search Report and Written Opinion for Application No. PCT/US2010/054637 dated Jan. 3, 2011.

International Search Report and Written Opinion for Application No. PCT/US2010/054684 dated Jan. 10, 2011.

Irigoyen, M.C.C. et al, Baroreflex Control of Sympathetic Activity in Experimental Hypertension, Brazilian Journal of Medical and Biological Research, (1998) 31: 1213-1220.

Izzo, Jr, Joseph L. et al, The Sympathetic Nervous System and Baroreflexes in Hypertension and Hypotension, Current Hypertension Reports 1999, 3:254-263.

Jackman, Warren M. et al, Catheter Ablation of Arrhythmias, Proposed Anatomy and Catheter Ablation of Epicardial Posteroseptal and Left Posterior Accessory AV Pathways (Chapter 16), 2002, Futura Publishing Company, Inc., 321-343.

Zazgornik, Jan et al, Bilateral Nephrectomy: The Best, but Often Overlooked, Treatment for Refractory Hypertension in Hemodialysis Patients, AJH 1998; 11:1364-1370.

Jaff, Michael R. et al, Kidney Stenting Lowers Blood Pressure in Patients with Severe Hypertension; Catheterization and Cardiovascular Interventions; Published Online: Jun. 27, 2012 (DOI: 10.1002/ccd.24449); Print Issue Date: Sep. 2012. URL: http://onlinelibrary.wiley.com/doi/10.1002/ccd.24449/abstract.

Jain, Mudit K. et al, A Three-Dimensional Finite Element Model of Radiofrequency Ablation with Blood Flow and Its Experimental Validation, Annals of Biomedical Engineering, vol. 28, pp. 1075-1084, 2000.

Jais, Pierre et al, Efficacy and Safety of Septal and Left-Atrial Linear Ablation for Atrial Fibrillation, The American Journal of Cardiology, vol. 84 (9A), Nov. 1999, 139R-146R.

Janssen, Ben J.A. et al, Frequency-Dependent Modulation of Renal Blood Flow by Renal Nerve Activity in Conscious Rabbits, American Journal of Physiology, 1997, 273:R597-R608.

Janssen, Ben J.A. et al, Renal Nerves in Hypertension, Miner Electrolyle Metab 1989;15:74-82.

Jin, Yu et al, No Support for Renal Denervation in a Meta-Analysis, JACC vol. 62, No. 21, 2013 Correspondence Nov. 19-26, 2013:2029-30.

Kaltenbach, Benjamin et al, Renal Artery Stenosis After Renal Sympathetic Denervation, J Am Coll Cardiel. Dec. 25, 2012;60(25):2694-5.

Kaltenbach, Benjamin et al, Renal Sympathetic Denervation as Second-Line Therapy in Mild Resistant Hypertension: A Pilot Study, Catheterization and Cardiovascular Interventions 81:335-339 (2013).

Kamiya, Atsunori et al, Parallel Resetting of Arterial Baroreflex Control of Renal and Cardiac Sympathetic Nerve Activities During Upright Tilt in Rabbits, Am J Physiol Heart Circ Physiol 298: H1966-H1975, 2010.

Kandzari, David E. et al, Catheter-Based Renal Denervation for Resistant Hypertension: Rationale and Design of the SYMPLICITY HTN-3 Trial, Clin. Cardiel. 35, 9, 528-535 (2012).

Kapural, Leonardo et al, Radiofrequency Ablation for Chronic Pain Control, Current Pain and Headache Reports 2001, 5:517-525.

Kassab, Salah et al, Renal Denervation Attenuates the Sodium Retention and Hypertension Associated with Obesity, Hypertension vol. 25, No. 4, Part Apr. 2, 1995.

Katholi, Richard E. et al, Decrease in Peripheral Sympathetic Nervous System Activity following Renal Denervation or Unclipping in the One-Kidney One-Clip Goldblatt Hypertensive Rat, The Journal of Clinical Investigation, Jan. 1982;69(1):55-62.

Katholi, Richard E. et al, Role of the Renal Nerves in the Pathogenesis of One-Kidney Renal Hypertension in the Rat, Hypertension. 1981;3:404-409.

Katholi, Richard E. et al, The Role of Renal Sympathetic Nerves in Hypertension: Has Percutaneous Renal Denervation Refocused Attention on Their Clinical Significance?; Progress in Cardiovascular Disease 52 (2009) 243-248.

Katritsis, Demosthenes et al, Recurrence of Left Atrium-Pulmonary Vein Conduction Following Successful Disconnection in Asymptomatic Patients, Europace (2004) 6, 425e432.

Killip 111 , Thomas, Oscillation of Blood Flow and Vascular Resistance During Mayer Waves, Circulation Research, vol. XI, Dec. 1962, 987-993.

Kingwell, Bronwyn A. et al, Assessment of Gain of Tachycardia and Bradycardia Responses of Cardiac Baroreflex, Am J Physiol Heart Circ Physiol 260:H1254-H1263, 1991.

Kirchheim, H. et al, Sympathetic Modulation of Renal Hemodynamics, Renin Release and Sodium Excretion, Klin Wochenschr (1989) 67: 858-864.

Klein, GE et al, Endovascular Treatment of Renal Artery Aneurysms with Conventional Non-Detachable Microcoils and Guglielmi Detachable Coils, Br J Ural. Jun. 1997; 79(6):852-860.

Knight, Eric L. et al, Predictors of Decreased Renal Function in Patients with Heart Failure During Angiotensin-Converting Enzyme Inhibitor Therapy: Results from the Studies of Left Ventricular Dysfunction (SOLVD), American Heart Journal, vol. 138, No. 5, Part 1, Nov. 1999, 849-855.

Koepke, John P. et al, Functions of the Renal Nerves, The Physiologist, vol. 28, No. 1, Feb. 1985, 47-52.

Kompanowska-Jezierska, Elzbieta et al, Early Effects of Renal Denervation in the Anaesthetised Rat: Natriuresis and Increased Cortical Blood Flow, Journal of Physiology (2001), 531.2, pp. 527-534.

Krum, Henry et al, Catheter-Based Renal Sympathetic Denervation for Resistant Hypertension: A Multicentre Safety and Proof-of-Principle Cohort Study, www.thelancel.com vol. 373 Apr. 11, 2009 1275-1281.

Krum, Henry et al, Device-Based Antihypertensive Therapy: Therapeutic Modulation of the Autonomic Nervous System, Circulation. 2011 ;123:209-215.

La Grange, Ronald G. et al, Selective Stimulation of Renal Nerves in the Anesthetized Dog: Effect on Renin Release During Controlled Changes in Renal Hemodynamics, Circulation Research, Journal of the American Heart Association, 1973;33:704-712.

(56) References Cited

OTHER PUBLICATIONS

Labeit, Alexander Michael et al, Changes in the Prevalence, Treatment and Control of Hypertension in Germany? A Clinical-Epidemiological Study of 50.000 Primary Care Patients, PLOS ONE, Dec. 2012, vol. 7, Issue 12, e52229, 1-11.

Labonte, Sylvain, Numerical Model for Radio-Frequency Ablation of the Endocardium and its Experimental Validation, IEEE Transactions on Biomedical Engineering, vol. 41, No. 2. Feb. 1994, 108-115.

Lambert, Gavin W. et al, Health-Related Quality of Life After Renal Denervation in Patients With Treatment-Resistant Hypertension, Hypertension. 2012;60:1479-1484.

Lee, Sang Joon et al, Ultrasonic Energy in Endoscopic Surgery, Yonsei Medical Journal, vol. 40, No. 6, pp. 545-549, 1999.

Leertouwer, Trude C. et al, In-Vitro Validation, with Histology, of Intravascular Ultrasound in Renal Arteries, Journal of Hypertension 1999, vol. 17 No. 2, 271-277.

Leishman, A.W.D., Hypertension—Treated and Untreated, British Medical Journal, May 1959, 1361-1368.

Leonard, Bridget L. et al, Differential Regulation of the Oscillations in Sympathetic Nerve Activity and Renal Blood Flow Following Volume Expansion, Autonomic Neuroscience: Basic and Clinical 83 (2000) 19-28.

Levin, Stephen, Ardian: Succeeding Where Drugs Fail Treating Hypertension in the Cath Lab, In Vivo: The Business & Medicine Report, vol. 27, No. 10, Nov. 2009.

Litynski, Grzegorz S., Kurt Semm and the Fight against Skepticism: Endoscopic Hemostasis, Laparoscopic Appendectomy, and Semm's Impact on the "Laparoscopic Revolution", JSLS. Jul.-Sep. 1998; 2(3): 309-313.

Lu, David S.K. et al, Effect of Vessel Size on Creation of Hepatic Radiofrequency Lesions in Pigs: Assessment of the "Heat Sink" Effect, American Journal of Radiology, 178, Jan. 2002, 47-51.

Luscher, Thomas F. et al, Renal Nerve Ablation After SYMPLICITY HTN-3: Confused at the Higher Level?; European Heart Journal, doi:10.1093/eurheartj/ehu195; May 14, 2014.

Lustgarten, Daniel L. et al, Cryothermal Ablation: Mechanism of Tissue Injury and Current Experience in the Treatment of Tachyarrhythmias, Progress in Cardiovascular Diseases, vol. 41, No. 6 (May/June), 1999: pp. 481-498.

Mahfoud, Felix et al, Expert Consensus Document from the European Society of Cardiology on Catheter-Based Renal Denervation, European Heart Journal, Jul. 2013;34(28):2149-57.

Mancia, Giuseppe et al, Sympathetic Activation in the Pathogenesis of Hypertension and Progression of Organ Damage, Hypertension Journal of the American Heart Association, 1999, 34:724-728.

McGahan, John P. et al, History of Ablation, Tumor Ablation, 2005, pp. 3-16.

Medtronic, Inc., J.P. Morgan Healthcare Conference, Corrected Transcript, Jan. 13, 2014, Factset:Callstreet, www.callstreet.com.

Medtronic, Inc., Medtronic Announces U.S. Renal Denervation Pivotal Trial Fails to Meet Primary Efficacy Endpoint While Meeting Primary Safety Endpoint, www.medtronic.com, Jan. 9, 2014.

Medtronic, Inc., RON Therapy with the Symplicity Renal Denervation System, Procedure Fact Sheet, www.medtronic.com, 2011.

Medtronic, Inc., Renal Denervation (RON) Novel Catheter-based Treatment for Hypertension, Symplicity RON System Common Q&A, 2011.

Medtronic, Inc., Scientific Basis Behind Renal Denervation for the Control of Hypertension, Dec. 2012, http://www.icimeeting.com/2012/images/stories/PD F/1448_Wilcox_I_Mon.pdf.

Mehdirad, Ali et al, Temperature Controlled RF Ablation in Canine Ventricle and Coronary Sinus using 7 Fr or 5 Fr Ablation Electrodes, PACE, vol. 21, Jan. 1998, Part 11, 316-321.

Meredith, I T et al, Exercise Training Lowers Resting Renal But Not Cardiac Sympathetic Activity in Humans; Hypertension Journal of the American Heart Association, 1991;18:575-582.

Michaelis, Lawrence L. et al, Effects of Renal Denervation and Renin Depletion on the Renal Responses to Intravascular Volume Expansion, Ann Surg. Mar. 1972; 175(3): 424-430.

Millard, F.C. et al, Renal Embolization for Ablation of Function in Renal Failure and Hypertension, Postgraduate Medical Journal (1989) 65, 729-734.

\* cited by examiner

ELECTRODE ASSEMBLY FOR CATHETER SYSTEM

CROSS-REFERENCE TO RELATED APPLICATION

This application is a divisional application of U.S. application Ser. No. 14/258,398, filed on Apr. 22, 2014, now abandoned, which claims priority to provisional application Ser. No. 61/842,646 filed Jul. 3, 2013, all above applications of which are incorporated herein by reference in their entireties.

BACKGROUND OF THE DISCLOSURE

A. Field of the Disclosure

The present disclosure relates generally to a catheter system for use in a human body, and more particularly to a multi-electrode catheter system, and even more particularly to an electrode assembly for a multi-electrode catheter system.

B. Background Art

Catheter systems are well known in the art for use in medical procedures, such as diagnostic, therapeutic and ablative procedures. Typical catheter systems generally include an elongate catheter extending from a handle. A physician manipulates the catheter through the patient's vasculature to an intended site within the patient. The catheter typically carries one or more working components, such as electrodes or other diagnostic, therapeutic or ablative devices for carrying out the procedures. One or more controls or actuators may be provided on the handle for selectively adjusting one or more characteristics of the working components.

One particular example of a multi-electrode catheter system is an ablative catheter system in which the working component is a multi-electrode component carried at the distal end of a flexible catheter. A control wire extends within the catheter from the multi-electrode component to the handle to operatively connect the multi-electrode component to an actuator on the handle. Manipulating the actuator acts on the control wire to configure the multi-electrode component into a desired configuration for carrying out the ablative procedure. For example, in one such ablative catheter system made by St. Jude Medical, Inc. under the trade name EnligHTN, the multi-electrode component is an electrode assembly in the general form of a basket. Upon locating the electrode basket at a desired location within the patient, manipulating the actuator associated with the handle pulls on the control wire to reconfigure the electrode basket from a collapsed configuration to an expanded configuration in which the electrodes are intended to be in apposition with a surface, such as an arterial wall of the patient. It is thus desirable to facilitate apposition of as many of the electrodes of the electrode basket as possible against the arterial wall of the patient when the electrode basket is expanded to achieve optimal performance of the multi-electrode catheter system.

BRIEF SUMMARY OF THE DISCLOSURE

In one embodiment, an electrode assembly for an electrode catheter system generally comprises first and second struts each extending from a proximal end to a distal end of the electrode assembly and having a corresponding electrode disposed thereon intermediate the proximal and distal ends of the electrode assembly. The electrode assembly is configurable between a collapsed configuration and an expanded configuration, with the electrodes being transversely spaced from the longitudinal axis of the electrode assembly a greater distance in the expanded configuration than in the collapsed configuration. In the collapsed configuration, the electrode on the first strut is at a first longitudinal position intermediate the proximal and distal ends of the electrode assembly and the electrode on the second strut is at a second longitudinal position intermediate the proximal and distal ends of the electrode assembly and different from the first longitudinal position of the electrode on the first strut. In the expanded configuration, the first longitudinal position of the electrode on the first strut is substantially equal to the second longitudinal position of the electrode on the second strut.

In another embodiment, an electrode assembly for an electrode catheter system generally comprises a plurality of struts each extending from a proximal end to a distal end of the electrode assembly. Each strut has a longitudinally extending proximal leg, a longitudinally extending distal leg, and a center segment extending between and interconnecting the proximal leg and the distal leg. The proximal leg and the distal leg of at least one of the struts has a corresponding stiffness, and the center segment of the at least one of the struts has a stiffness greater than the stiffness of each of the proximal leg and the distal leg of the at least one of the struts. The center segment of each of the struts has a corresponding electrode thereon. The electrode assembly is configurable between a collapsed configuration and an expanded configuration, with the electrodes being transversely spaced from the longitudinal axis of the electrode assembly a greater distance in the expanded configuration than in the collapsed configuration.

In yet another embodiment, an electrode assembly for an electrode catheter system generally comprises a plurality of struts each extending from a proximal end to a distal end of the electrode assembly. Each strut has a longitudinally extending proximal leg, a longitudinally extending distal leg, and a center segment extending between and interconnecting the proximal leg and the distal leg. The center segment of each of the struts has a corresponding electrode thereon. The electrode assembly is configurable between a collapsed configuration and an expanded configuration, with the electrodes being transversely spaced from the longitudinal axis of the electrode assembly a greater distance in the expanded configuration than in the collapsed configuration.

In still another embodiment, an electrode assembly for an electrode catheter system generally comprises a plurality of struts each extending from a proximal end to a distal end of the electrode assembly. Each strut has a riser element disposed thereon intermediate the proximal end and the distal end of the electrode assembly. The electrode assembly is configurable between a collapsed configuration and an expanded configuration. In the expanded configuration the riser element of each strut extends transversely outward from the longitudinal axis of the electrode assembly a greater distance than any other point along the respective strut, with each strut further having an electrode disposed on the respective riser element.

In still another embodiment, an electrode assembly for an electrode catheter system generally comprises a plurality of struts each extending from a proximal end to a distal end of the electrode assembly and each having a corresponding electrode thereon. The electrode assembly is configurable between a collapsed configuration and an expanded configuration, with the electrodes being transversely spaced from the longitudinal axis of the electrode assembly a greater distance in the expanded configuration than in the collapsed configuration. In the collapsed configuration at least one of the struts has a generally concave segment extending lengthwise along the strut intermediate the proximal and distal ends of the electrode assembly.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings.

DETAILED DESCRIPTION OF THE DISCLOSURE

Figure 1:
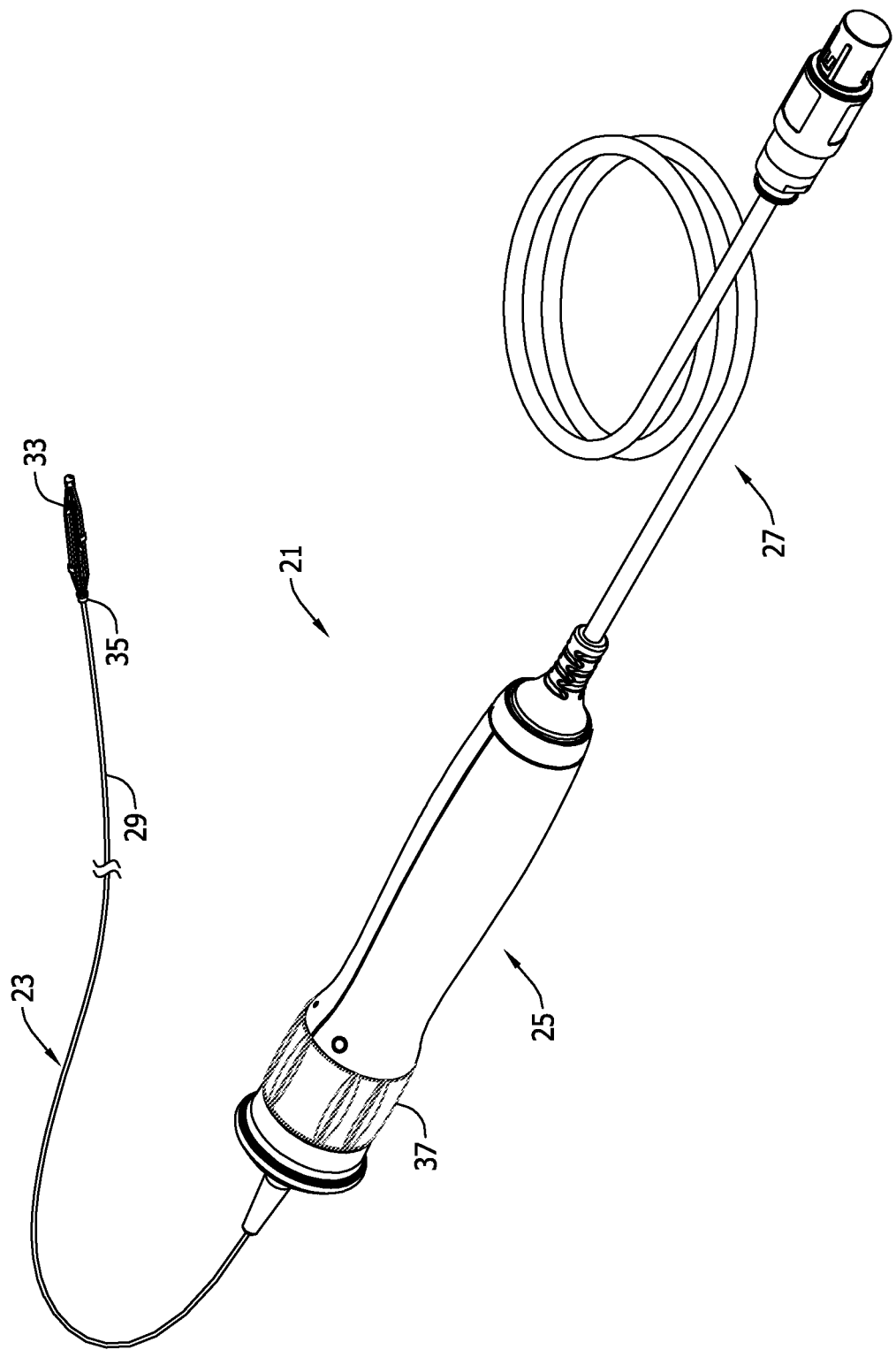
FIG. 1 is a perspective view of one embodiment of a catheter system including a handle, a catheter and an electrode assembly having multiple electrodes, with the electrode assembly being in what is referenced herein as a collapsed configuration.
Figure 2:
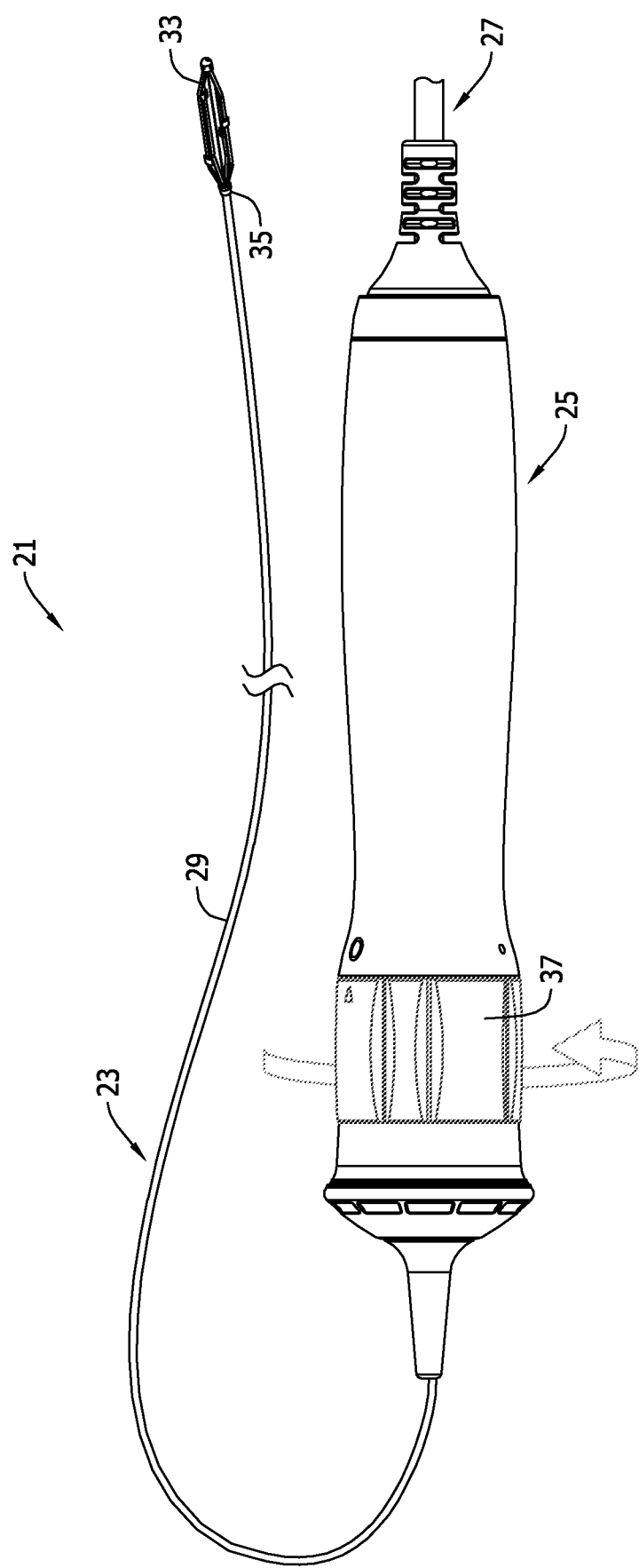
FIG. 2 is a side elevation of the catheter system of FIG. 1, with the electrode assembly being in what is referenced herein as an expanded configuration resulting from rotation of a rotatable actuator.

Referring now to the drawings, and in particular to FIGS. 1 and 2, one embodiment of a catheter system 21 includes a flexible catheter 23, a handle 25 to which the catheter is connected, and a conductor assembly 27 for electrically connecting the catheter system to a suitable power supply (not shown). As one example, the catheter system 21 illustrated and described herein is suitably constructed for use as an ablation system, such as a renal or heart ablation system. More particularly, the illustrated catheter system 21 is a multi-electrode renal denervation system. One example of such a catheter system 21 is currently made by St. Jude Medical, Inc. under the trade name EnligHTN. General operation of a multi-electrode renal denervation system is known to those of skill in the art and is not described further herein except to the extent necessary to describe the present embodiments. It is also understood that the catheter system 21 may be used for any other suitable treatment or purpose without departing from the scope of this disclosure. Additionally, while the catheter system 21 is illustrated and described herein as including a flexible catheter 23, the system may further include other components used, for example, to guide the flexible catheter into the patient—such as, without limitation, a relatively more rigid guide catheter (not shown), or an over-the-wire system (not shown).

The catheter 23 includes an elongate, flexible hollow shaft 29 connected to the handle 25 at or near a proximal or rear end of the catheter shaft (not shown because it is hidden by a connector at the front end of the handle 25), and an electrode assembly 33 disposed at or near a distal or front end 35 of the catheter shaft. It is understood, however, that the electrode assembly 33 may be disposed anywhere along the catheter shaft 29 intermediate the proximal end and the distal end 35 thereof without departing from the scope of this disclosure. As used herein, the terms proximal and front, and distal and rear, are used with reference to the orientation of the catheter system 21 illustrated in the various drawings and for the purpose of describing the various embodiments set forth herein, and are not intended as limiting the catheter system and related components to having any particular orientation upon assembly or during operation thereof. In particular, the terms proximal and rear refer to a longitudinal position that is relatively nearer to the handle 25 while the terms distal and front refer to a longitudinal position that is relatively farther from the handle.

The illustrated electrode assembly 33 is in the form of what may be referred to as an electrode basket and is suitably configurable between a collapsed configuration (FIGS. 1 and 3) for maneuvering and positioning the electrode assembly in the patient, and an expanded configuration (FIGS. 2 and 5) for operation of the electrode assembly to perform a desired procedure such as an ablation procedure. An annular (e.g., ring-shaped) actuator 37 is mounted on the handle 25 for rotation relative thereto and is operatively connected to the electrode assembly 33 for selectively configuring the electrode assembly between its collapsed and expanded configurations. It is understood that another suitable actuator (e.g., slide, push button, lever, etc.) may be used instead of the rotating actuator 37 to selectively configure the electrode assembly 33 without departing from the scope of this disclosure. In some embodiments, the electrode assembly 33 may be selectively adjustable between an infinite number of configurations (e.g., degrees of expansion) between its collapsed and expanded configurations using the actuator 37.

A control line, such as a suitable cable or pull wire 41 (FIGS. 3 and 4) extends from the electrode assembly 33 within the hollow catheter shaft 29 and into the handle 25 for operative connection with the actuator to thereby operatively connect the actuator 37 with the electrode assembly. In some embodiments, two or more pull wires, cables or other suitable control lines may be used for selectively configuring the electrode assembly 33. It is also understood that the control line 41 may be any suitable control line other than a pull wire, such as a cable, string, tie, compression member or other suitable control to operatively connect the electrode assembly 33 to the actuator 37. In other embodiments, any suitable conventional manner for actuating or otherwise selectively configuring the electrode assembly 33 may be used. A suitable twisted electrical wire bundle (not shown) also extends through the hollow catheter shaft 29 from the handle to the electrode assembly to deliver power to the electrode assembly.

Figure 3:
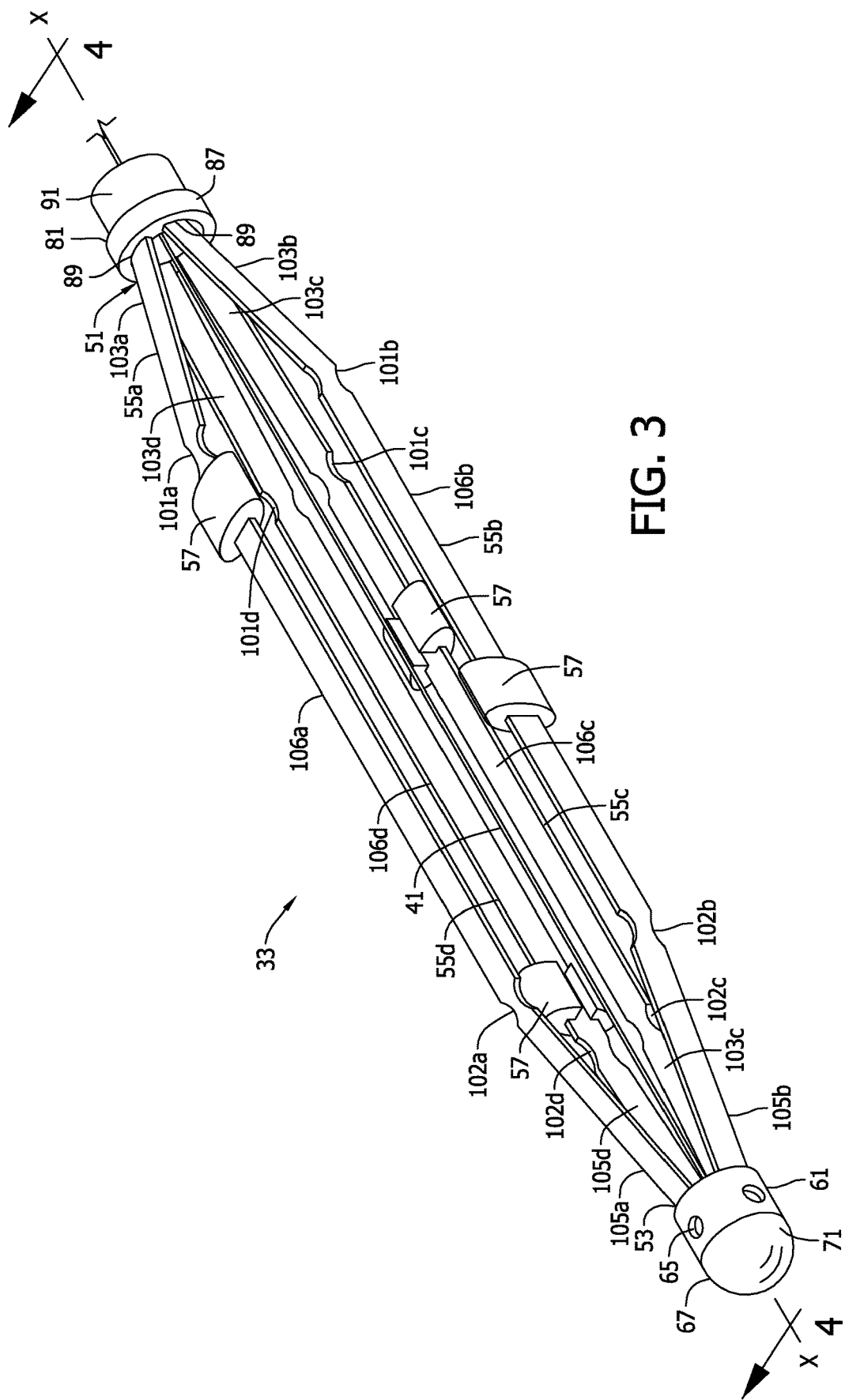
FIG. 3 is a perspective view of the electrode assembly of FIG. 1 with a plurality of struts carrying the multiple electrodes, the electrode assembly being in its collapsed configuration.

With reference now to FIG. 3, the electrode assembly 33 has a proximal end 51 at which the assembly is connected to the catheter shaft 29 (e.g., to the distal end 35 of the catheter shaft in the embodiment of FIGS. 1 and 2), a distal end 53 that in the illustrated embodiment also defines a distal end, or tip, of the catheter 23, and a longitudinal axis X. The illustrated electrode assembly 33 comprises a set of four struts 55a-d, extending coextensively with each other from the proximal end 51 to the distal end 53 of the electrode assembly in circumferentially equal spaced relationship with each other about the longitudinal axis X of the electrode assembly. In other embodiments, the electrode assembly 33 may comprise more or less than four struts 55a-d (see, e.g., the embodiments of FIGS. 32-38) without departing from the scope of this disclosure. It is also contemplated that the struts 55a-d may be other than equally spaced from each other circumferentially, and/or the struts may be other than coextensive with each other, and remain within the scope of this disclosure.

Each of the struts 55a-d carries at least one electrode 57 disposed at a respective longitudinal position along the strut, i.e., at a respective longitudinal distance along the longitudinal axis X from the proximal end of the electrode assembly. In the embodiment of FIG. 3, each of the electrodes 57 is at a different longitudinal position. It is understood that the electrodes 57 may be at longitudinal positions other than those shown in FIG. 3. In other embodiments, two, three or all of the electrodes 57 may instead be at the same longitudinal position. It is also understood that multiple electrodes 57 may be carried by any one or all of the struts 55a-d, e.g., with the electrodes on any given strut spaced longitudinally from each other along the strut. While not shown in FIG. 3, a respective suitable sheathing or sleeve, constructed of a polymeric material, circumferentially encloses each of the struts 55a-d along their respective lengths. The segment of the control line 41 that extends from the proximal end to the distal end of the electrode assembly may likewise be circumferentially enclosed by a suitable polymeric sheathing or sleeve.

Figure 4:
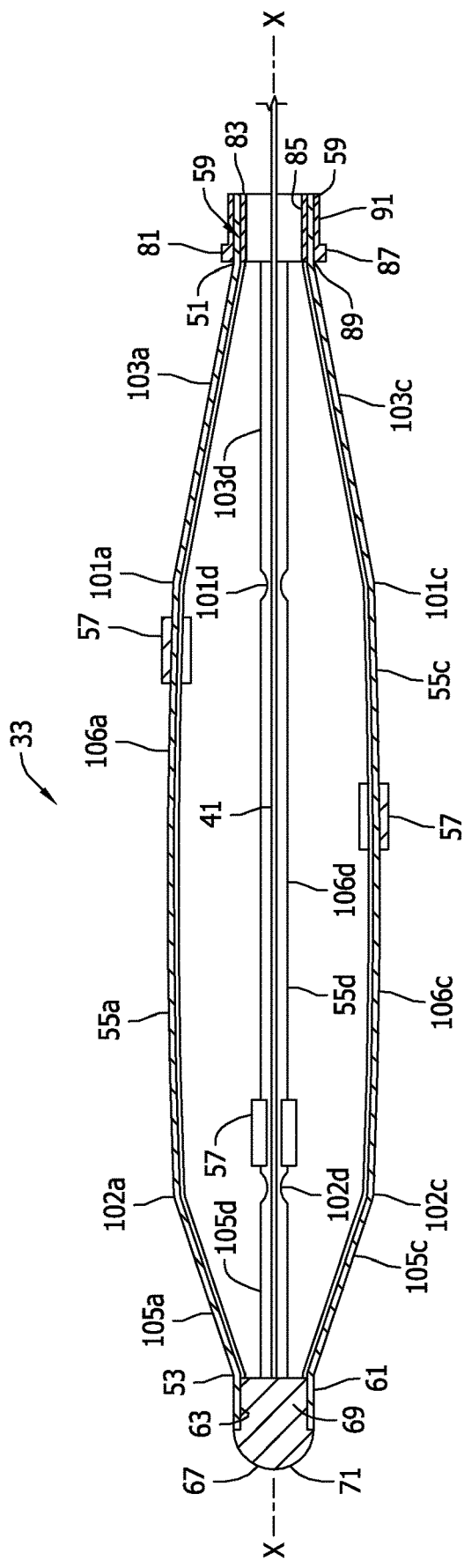
FIG. 4 is a longitudinal cross-section of the electrode assembly of FIG. 3.
Figure 6:
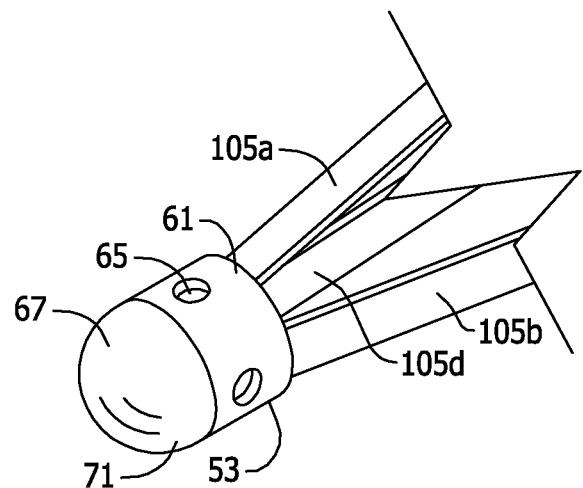
FIG. 6 is an enlarged perspective view of a distal end of the electrode assembly of FIG. 3.

At the distal end 53 of the electrode assembly 33, the struts 55a-d terminate at, and in one embodiment for making the electrode assembly are formed integrally with, a connecting ring 61 (as best illustrated in FIGS. 4 and 6) having a central opening 63 that is coaxial with the longitudinal axis X of the electrode assembly. In the illustrated embodiment, multiple holes 65 are formed in the sidewall of the connecting ring 61 in spaced relationship with each other about the circumference of the connecting ring and are open to the central opening 63 of the connector. In other embodiments, however, the holes 65 may be omitted. Suitable polymeric sheathing (not shown) may surround the connecting ring 61 to cover the holes 65 following assembly of the electrode assembly 33. A blunt tip 67 includes a rounded head 71 having a cylindrical body 69 extending longitudinally therefrom and being generally hollow along its length such that the rounded head closes the distal end of the body.

The control line 41 extends generally along the longitudinal axis X of the electrode assembly 33 through the body 69 of the tip 67 where it is secured to the tip by braising, adhesive, welding, soldering or other suitable securement technique. The tip body 69 is sized in transverse cross-section, e.g., outer diameter, to be received through and seated within the central opening 63 of the connecting ring 61 with the head 71 of the tip 67 abutting against the end of the connecting ring as seen in FIGS. 4 and 6. The holes 65 spaced about the circumference of the connecting ring 61 allow a suitable adhesive to be supplied through the holes for securing the tip 67 on the connecting ring—thereby connecting the distal end 53 of the electrode assembly 33 to the control line 41 for operative connection with the actuator 37 on the handle 25. In other embodiments, the struts 55a-d may be retained at the distal end 53 of the electrode assembly 33 in another suitable manner and remain within the scope of this disclosure. It is also contemplated that the struts 55a-d and connecting ring 61 may be formed separate from each other and subsequently secured together by any suitable securement technique.

Figure 7:
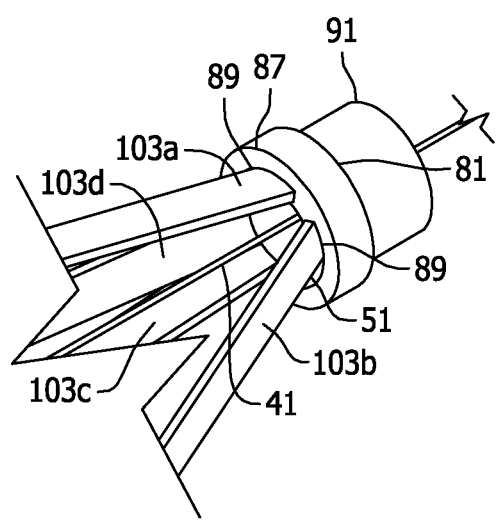
FIG. 7 is an enlarged perspective view of a proximal end of the electrode assembly of FIG. 3.
Figure 8:
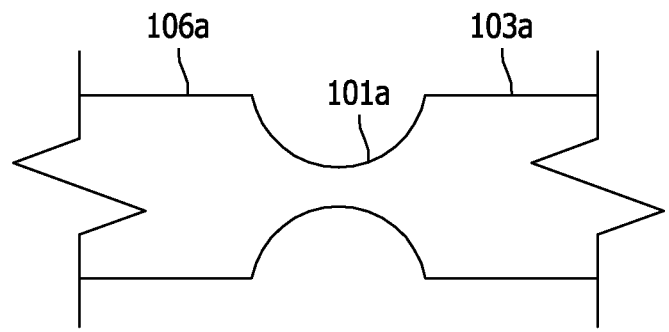
FIG. 8 is an enlarged top plan view of another embodiment of a hinge suitable for use with the electrode assembly of FIG. 3.

Referring to FIGS. 4 and 7, at the proximal end 51 of the electrode assembly 33, longitudinal end segments 59 of the struts 55a-d are connected to the catheter shaft 29 by a suitable bushing 81. The bushing 81 includes a tubular cylindrical body 83 having a central opening 85 through which the control line 41 extends from the catheter shaft 29 to the electrode assembly 33. An annular flange 87 extends radially outward from the longitudinally outer end of the bushing 81. The flange 87 has four slots 89 (corresponding to the respective longitudinal end segments 59 of the struts 55a-d) extending longitudinally therethrough radially outward of the cylindrical body 83 of the bushing 81 and in circumferentially spaced relationship with each other. The longitudinal end segments 59 of the struts 55a-d extend through the respective slots 89 and along the outer surface of the cylindrical body 83 of the bushing 81.

The body 83 of the bushing 81 (along with the longitudinal end segments 59 of the struts 55a-d) is fitted with a polyimide sleeve 91 filled with suitable adhesive to secure the sleeve and longitudinal end segments of the struts to the bushing. The bushing 81, struts 55a-d and polyimide sleeve 91 are inserted into the distal end 35 of the hollow catheter shaft 29 and secured to the catheter shaft by suitable adhesive to secure the proximal end 51 of the electrode assembly 33 to the distal end of the catheter shaft. It is understood that the struts 55a-d may be connected to the catheter shaft 29 by any other suitable connection that allows the electrode assembly 33 to function in the manner described herein.

Figure 5:
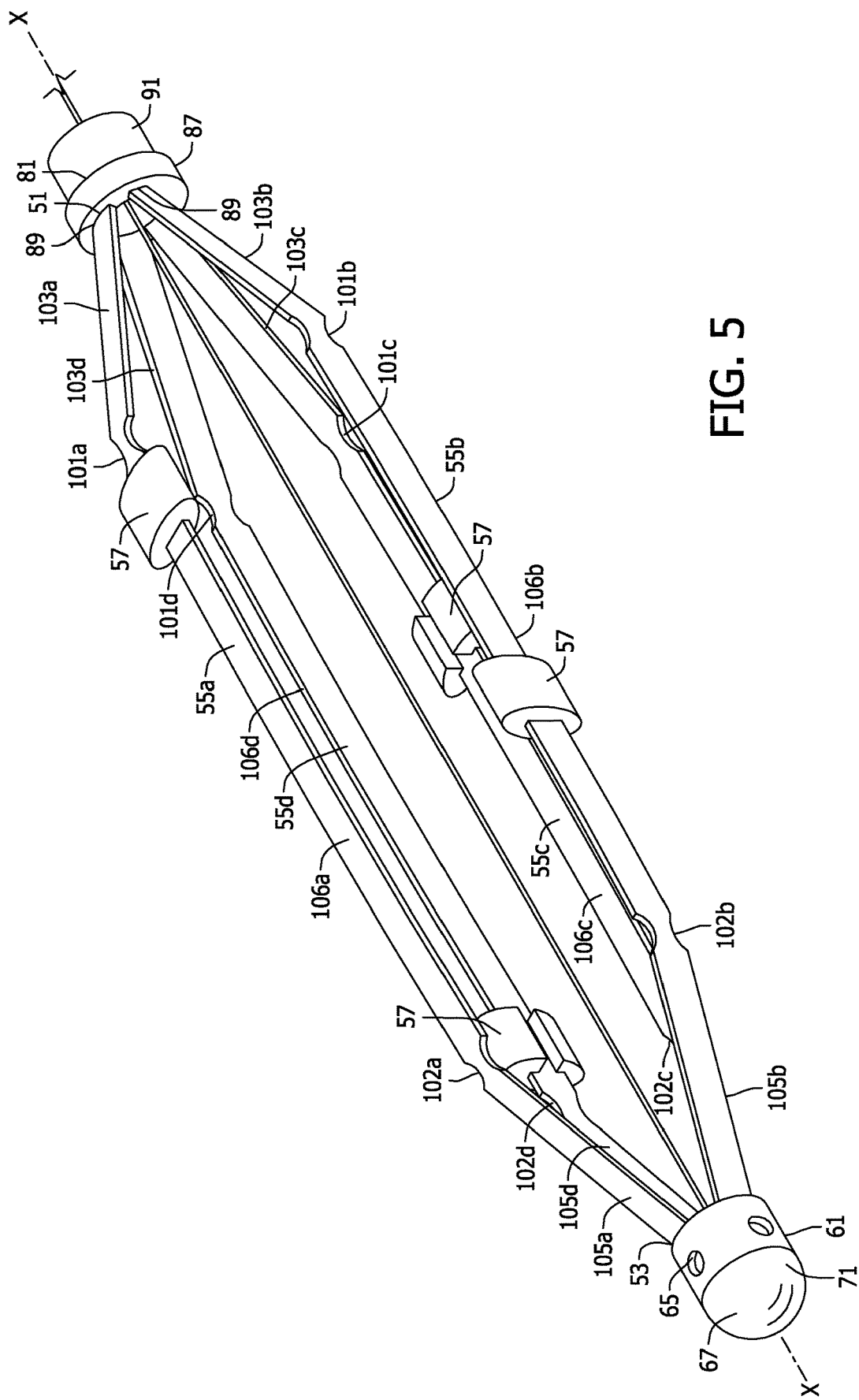
FIG. 5 is a perspective view of the electrode assembly similar to FIG. 3 but illustrating the electrode assembly in its expanded configuration.

The electrode assembly 33 thus has a length defined by the distance along the longitudinal axis X from the proximal end 51 to the distal end 53 of the electrode assembly. To configure the electrode assembly 33 from its collapsed configuration (e.g., as illustrated in FIGS. 1 and 3) to its expanded configuration (e.g., as illustrated in FIGS. 2 and 5), rotation of the actuator 37 relative to the handle 25 operatively pulls on the control wire 41 to thereby pull the tip (i.e., the distal end 53) of the electrode assembly toward the proximal end 51 of the electrode assembly along the longitudinal axis X thereof. As the distance between the distal end 53 and the proximal end 51 of the electrode assembly 33 is shortened (i.e., as the length of the electrode assembly decreases), the struts 55a-d are longitudinally compressed and thus forced to bend, or flex transversely outward away from the longitudinal axis X of the electrode assembly to form the expanded configuration of the electrode assembly. As used herein, the expanded configuration of the electrode assembly refers to any transverse movement of the struts 55a-d outward from the collapsed (e.g., initial or pre-set) configuration of the electrode assembly, and may be variably adjusted. Accordingly, it is understood that in the expanded configuration the electrode assembly 33 may be expanded more or less than as illustrated in the various embodiments herein. It is also understood that the collapsed configuration is not intended to mean the most compressed form in which the electrode assembly 33 may be configured, but rather it refers to the relaxed configuration of the electrode assembly free from any external compression forces (such as when compressed to fit the electrode assembly into a guide tube or lumen).

Figure 21:
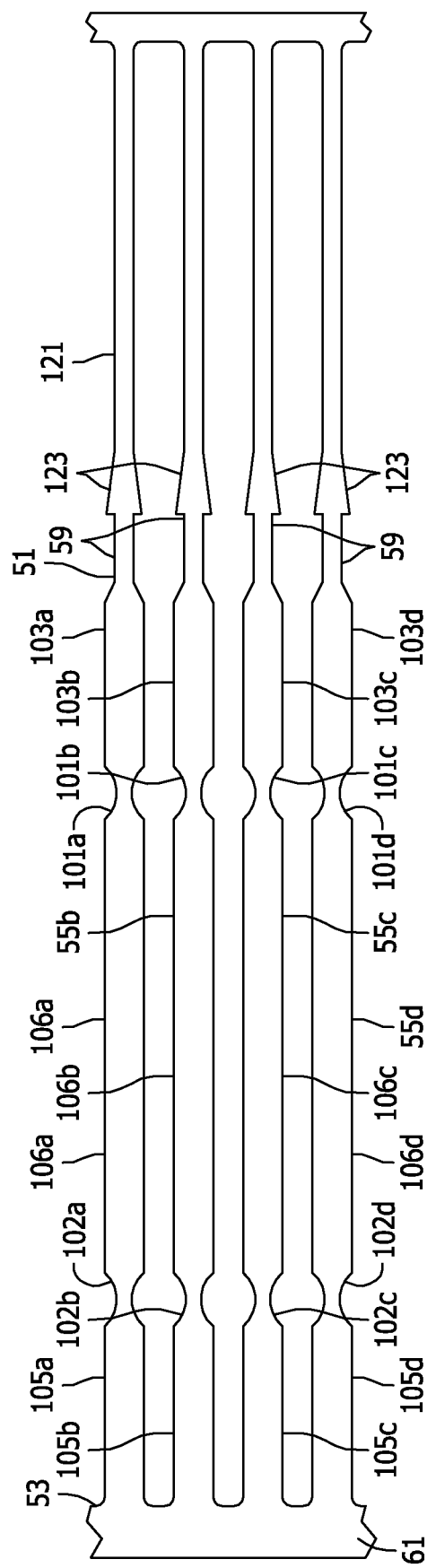
FIG. 21 is a schematic view of the electrode assembly of FIG. 3 at one stage of manufacturing thereof at which the electrode assembly is in the form of a tube, with the tube being in a longitudinally opened and laid flat orientation for illustrative purposes.

FIG. 21 illustrates one embodiment of a method for making the electrode assembly 33 of FIGS. 1-7. A unitary tube 121 of a material having sufficient strength and shape memory characteristics, such as Nitinol™, is used. The material or materials from which the tube 121 is constructed, however, may be any other suitable material and remain within the scope of this disclosure. In FIG. 21, the tube 121 is cut lengthwise and laid flat for illustrative purposes. The desired pattern of struts 55a-d is laser cut into the tube 121. As illustrated in FIG. 21, the tube 121 is initially longer than the length of the finished electrode assembly 33 (as illustrated, e.g., in FIG. 3). An alignment member 123 is formed on each strut 55a-d during the laser cutting process longitudinally outward of the ends of the struts near what eventually becomes the proximal end 51 of the electrode assembly 33.

Once the struts 55a-d are formed in the tube 121, an initial slight amount of preset expansion is formed in the tube 121 as illustrated in FIG. 3 using an internal and external die assembly or other suitable technique and then heat setting the tube to give the tube shape its collapsed (e.g., initial or preset) configuration. Such preset gives the struts 55a-d increased shaped memory and facilitates more predictable bending of the struts into the desired expanded configuration of the electrode assembly. Following the heat setting, the tube 121 is cut adjacent the alignment members 123 to define the longitudinal end segments 59 of the struts 55a-d for connecting the struts to the bushing 81 and subsequently to the catheter shaft 29 in the manner described previously. The tip 67 is secured to the distal end 53 of the electrode assembly 33 (e.g., to the connecting ring 61) in the manner described previously.

With reference back to FIGS. 3 and 4 as well as to FIG. 21, each of the struts 55a-d of the illustrated electrode assembly 33 is suitably configured in at least the collapsed configuration of the electrode assembly to have what is referred to herein as a proximal leg 103a-d, a distal leg 105a-d, and a center segment 106a-d extending between and interconnecting the proximal and distal legs of the strut. To facilitate predictable bending of the struts 55a-d, each strut includes a pair of hinges 101a-d, 102a-d in longitudinally spaced relationship with each other, i.e., with one hinge 101a-d intermediate and interconnecting the proximal leg 103a-d and the center segment 106a-d of the strut and the other hinge 102a-d intermediate and interconnecting the distal leg 105a-d and the center segment of the strut. In particular, with reference to the strut 55a in FIG. 3, the proximal leg 103a extends from the one hinge 101a to the proximal end of the electrode assembly 33 and the distal leg 105a extends from the other hinge 102a to the connecting ring 61 at the distal end of the electrode assembly.

In the illustrated embodiment, the proximal leg 103a-d and the distal leg 105a-d of each strut 55a-d are of generally equal length. In other embodiments, some of which are described later herein, the proximal leg 103a-d and the distal leg 105a-d may be of unequal length. Also, in the illustrated embodiment, each strut 55a-d has a proximal leg 103a-d, central segment 106a-d and distal leg 105a-d of lengths equal to the proximal leg, central segment and distal leg of each of the other struts so as to maintain symmetry of the electrode assembly 33. It is understood, though, that the respective lengths of the proximal leg 103a-d, center segment 106a-d and distal leg 105a-d of one strut may be different from that of one or more of the other struts. The electrodes 57 are disposed respectively on the center segment 106a-d of each corresponding strut 55a-d.

In the illustrated embodiment of FIGS. 3 and 21, the proximal leg 103a-d, the distal leg 105a-d and the center segment 106a-d each have a uniform width along the respective lengths thereof, i.e., other than where the proximal leg narrows to form the end segments 59 that connect to the bushing 81. However, it is contemplated that in other embodiments the proximal leg 103a-d may have a non-uniform width, such as a width that decreases continuously (i.e., tapers or narrows) from adjacent the hinge 101a-d to the end segment 59. Alternatively, or additionally, the distal legs 105a-d may have a non-uniform width, such as a width that decreases continuously (i.e., tapers, or narrows) from adjacent the hinge 102a-d to adjacent the connecting ring 61. In other embodiments, the width of each proximal leg 103a-d and/or distal leg 105a-d may be tapered in another suitable manner. The width of each center segment 106a-d of each strut 55a-d is generally uniform along its length. Each strut 55a-d of the illustrated embodiment has a narrowed width intermediate the center segment 106a-d and the proximal leg 103a-d to define the hinge 101a-d and another narrowed width intermediate the center segment and the distal leg 105a-d to define the hinge 102a-d. In the illustrated embodiment the width of each strut 55a-d at the hinge 101a-d is equal to the width of the strut at the other hinge 102a-d. However, in other embodiments the width of the strut 55a-d at the hinge 101a-d may be different from the width of the strut at the other hinge 102a-d and remain within the scope of this disclosure.

As used herein, the term "hinge" refers to any suitable intended, preset or predetermined point or zone of flexure or bending in the strut. For example, in the illustrated embodiment of FIG. 3, the hinges 101a-d, 102a-d are each formed by generally U-shaped symmetrical cut-outs on opposite sides of each strut 55a-d so that the strut material is continuous across the narrowed width of the strut. The rounded contour of each of the cut-outs reduces the stress at the hinge 101a-d, 102a-d upon bending of the strut 55a-d.

Figure 9:
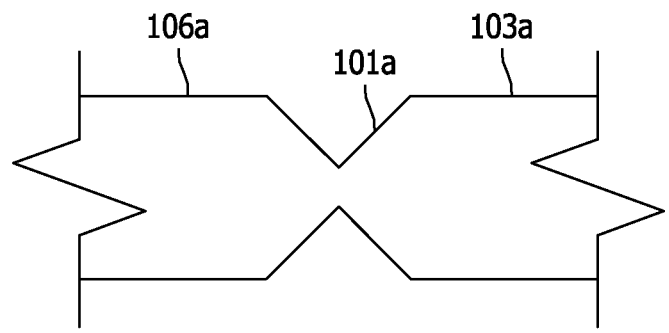
FIG. 9 is an enlarged top plan view of a third embodiment of a hinge suitable for use with the electrode assembly of FIG. 3.
Figure 10:
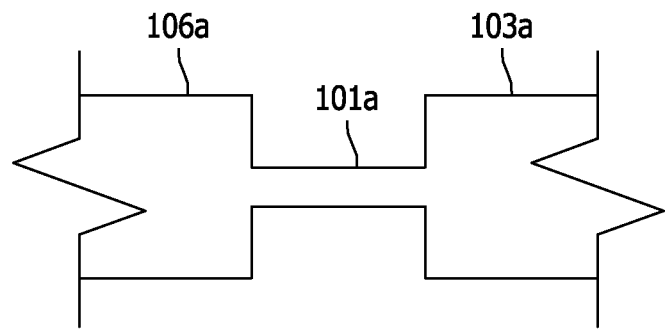
FIG. 10 is an enlarged top plan view of a fourth embodiment of a hinge suitable for use with the electrode assembly of FIG. 3.
Figure 11:
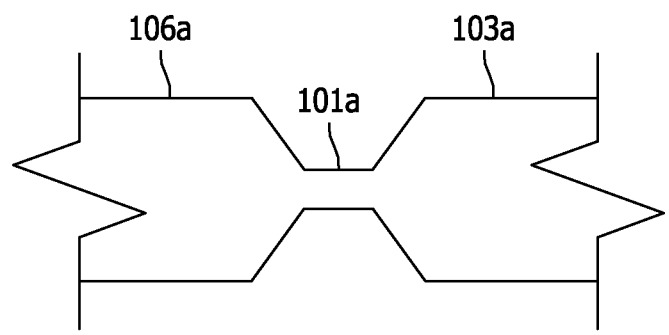
FIG. 11 is an enlarged top plan view of a fifth embodiment of a hinge suitable for use with the electrode assembly of FIG. 3.
Figure 12:
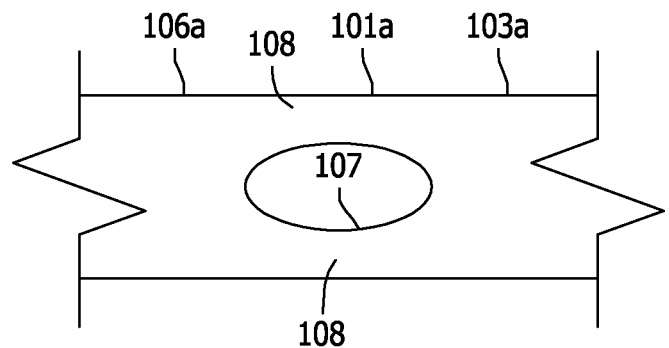
FIG. 12 is an enlarged top plan view of a sixth embodiment of a hinge suitable for use with the electrode assembly of FIG. 3.
Figure 13:
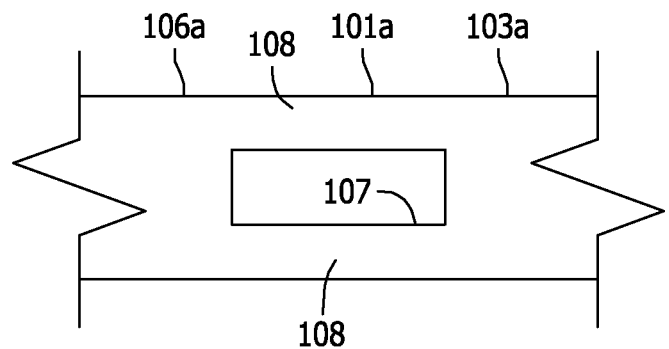
FIG. 13 is an enlarged top plan view of a seventh embodiment of a hinge suitable for use with the electrode assembly of FIG. 3.
Figure 14:
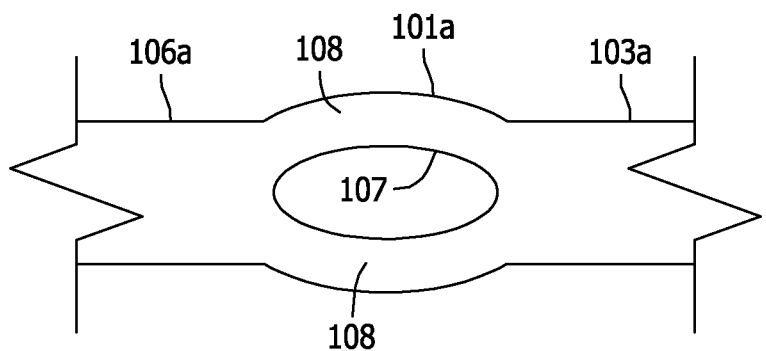
FIG. 14 is an enlarged top plan view of an eighth embodiment of a hinge suitable for use with the electrode assembly of FIG. 3.
Figure 15:
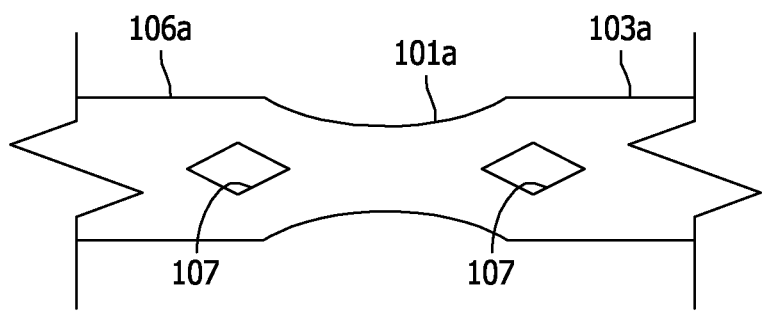
FIG. 15 is an enlarged top plan view of a ninth embodiment of a hinge suitable for use with the electrode assembly of FIG. 3.
Figure 16:
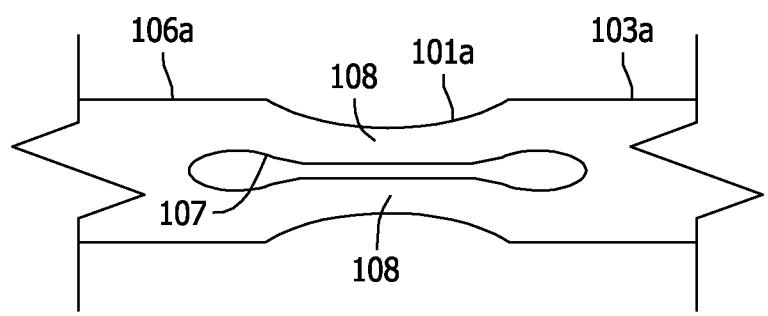
FIG. 16 is an enlarged top plan view of a tenth embodiment of a hinge suitable for use with the electrode assembly of FIG. 3.
Figure 17:
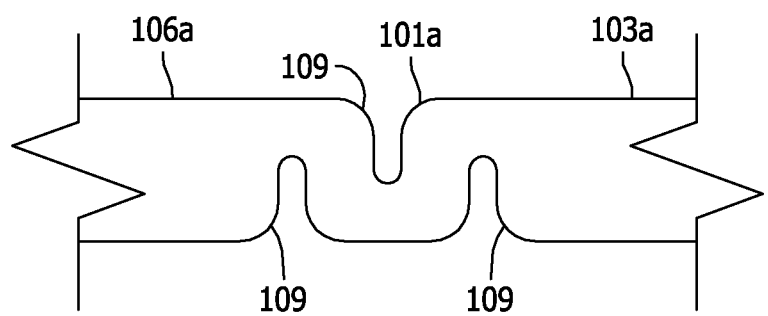
FIG. 17 is an enlarged top plan view of an eleventh embodiment of a hinge suitable for use with the electrode assembly of FIG. 3.

In other embodiments, such as illustrated in FIGS. 9-11, the hinges 101a-d, 102a-d (only one such hinge being illustrated) may be formed by symmetrical cut-outs that are other than generally U-shaped, such as generally V-shaped (FIG. 9), generally rectangular (FIG. 10), generally trapezoidal (FIG. 11) or other suitable shape. It is also understood that one or both of the hinges 101a-d, 102a-d may alternatively be formed by one or more interior openings 107 disposed between the side edges of the strut 55a-d at the respective hinge so that the narrowed width of the strut at the hinge is defined by the combined widths of the transverse webs 108 of strut material remaining on both sides of such an opening. For example, as illustrated in the alternative embodiments of FIGS. 12 and 13, such an interior opening 107 may be circular, oval (FIG. 12), rectangular (FIG. 13) or other suitable shape. In the alternative embodiment of FIG. 14, the strut is widened at the hinge 101a-d, 102a-d to accommodate an interior opening 107 having a generally ovate shape. FIGS. 15 and 16 illustrate another alternative embodiment in which each hinge 101a-d, 102a-d comprises opposed, symmetrical cut-outs along with one or more interior openings 107. In particular, in FIG. 15 a pair of generally diamond-shaped interior openings 107 are formed in each strut 55a-d adjacent the longitudinally opposite ends of the opposed cut-outs, while in FIG. 16 a single elongated interior opening 107 extends lengthwise from adjacent one end of the opposed cut-outs to adjacent the opposite end of the opposed cut-outs. It is contemplated that in other embodiments the opposed cut-outs may not be symmetrical.

Figure 18:
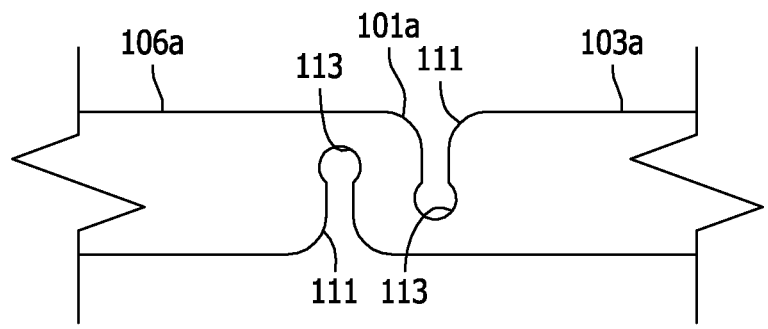
FIG. 18 is an enlarged top plan view of a twelfth embodiment of a hinge suitable for use with the electrode assembly of FIG. 3.
Figure 19:
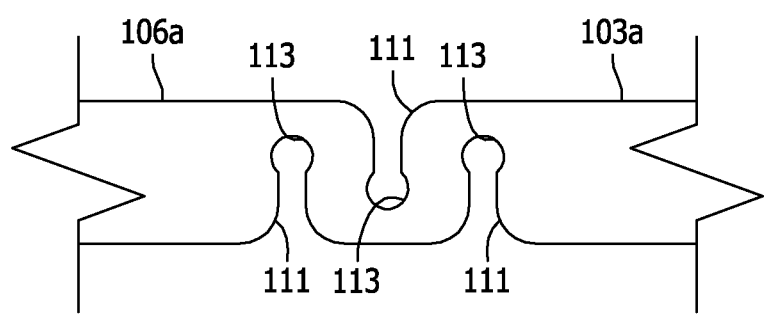
FIG. 19 is an enlarged top plan view of a thirteenth embodiment of a hinge suitable for use with the electrode assembly of FIG. 3.
Figure 20:
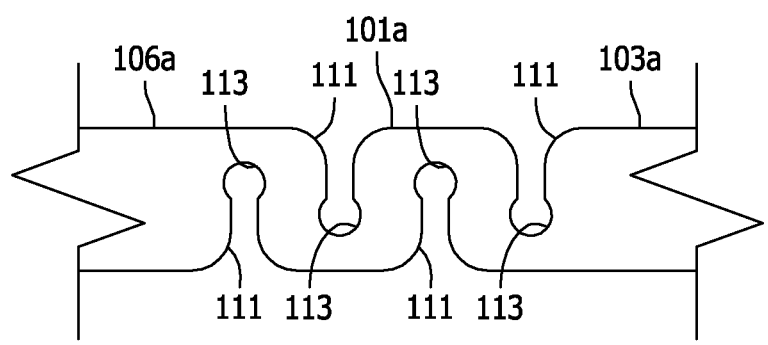
FIG. 20 is an enlarged top plan view of a fourteenth embodiment of a hinge suitable for use with the electrode assembly of FIG. 3.

FIGS. 17-20 illustrate additional alternative embodiments in which each hinge 101a-d, 102a-d is formed by two or more slots or cuts 109 extending transversely across the strut from opposite side edges of the strut. For example, in FIG. 17, a series of three generally V-shaped cuts 109 are formed in the side edges of the strut 55a-d—i.e., with two of the V-shaped cuts extending from one side edge of the strut transversely across part of the strut and the other V-shaped cut extending from the opposite side of the strut transversely across part of the strut intermediate the other two V-shaped cuts. The cuts 109 may be other than V-shaped in other embodiments. FIGS. 18, 19 and 20 illustrate slots 111, each having a generally circular terminal end 113, extending transversely across part of the strut 55a-d from opposite side edges thereof. For example, two such slots 111 are illustrated in FIG. 18, three such slots are illustrated in FIG. 19 and four such slots are illustrated in FIG. 20. It is understood that the number of slots 111 may be less than two or greater than four within the scope of this disclosure. It is also understood that the slots 111 may be shaped other than as illustrated and remain within the scope of this disclosure.

It is also contemplated that in other embodiments one or both of the hinges 101a-d, 102a-d of each strut 55a-d may be formed other than by forming cut-outs or slots in the struts. For example, in some embodiments one or all of the struts 55a-d may be of uniform width and cross-section along its entire length, but have a pair of longitudinally spaced preset bends or creases formed in the strut to respectively define the hinges 101a-d, 102a-d. In still other embodiments, a hinge 101a-d, 102a-d may be formed as a result of differing characteristics (e.g., transverse cross-section, thickness, width, etc.) between the proximal leg 103a-d and the center segment 106a-d and/or between the distal leg 105a-d and the center segment.

With reference to FIG. 5, by facilitating bending of the struts 55a-d at the respective hinges 101a-d, 102a-d in the expanded configuration of the electrode assembly 33, the center segment 106a-d of each strut has only a slight arch as illustrated, and in some embodiments may be substantially flat along its length. As such, while the electrodes 57 are at different longitudinal positions along the length of the electrode assembly 33, the relatively little to no arch in each of the center segments 106a-d of the struts 55a-d facilitates concurrent apposition of all of the electrodes against the arterial wall while still accommodating a relatively compact configuration (due to the longitudinally different positions of the electrodes) in the collapsed configuration of the electrode assembly, and more particularly when the electrode assembly is further compressed transversely from the collapsed position for maneuvering of the catheter within the patient—such as within a guide tube or lumen.

In some embodiments, at least the center segments 106a-d, the proximal and distal legs 103a-d, 105a-d and/or the hinges 101a-d, 102a-d are suitably configured to further facilitate the center segments 106a-d of the struts 55a-d having relatively little to no arch upon configuration of the electrode assembly 33 in its expanded configuration. For example, in one embodiment the center segments 106a-d, and optionally the proximal and distal legs 103a-d, 105a-d may each have a width in the range of about 0.018 inches to about 0.038 inches. Additionally, or alternatively, the center segments 106a-d, and optionally the proximal and distal legs 103a-d, 105a-d may each have a thickness in the range of about 0.003 inches to about 0.007 inches. It is understood, however, that the widths and/or thicknesses of the strut elements may be other than within the above ranges and remain within the present disclosure.

In addition to providing a relatively stiffened center segment, the hinges 101a-d, 102a-d may be relatively more flexible, such as by forming each hinge to have a width that is substantially less than the width of the center segments 106a-d and the proximal and distal legs 103a-d, 105a-d, to facilitate bending at the hinges instead of along the center segment. For example, relative to the range of widths set forth above for the center segments 106a-d and the proximal and distal legs 103a-d, 105a-d, the hinges 101a-d, 102a-d may each have a width in the range of about 0.008 inches to about 0.018 inches. It is understood, however, that the hinges 101a-d, 102a-d may have a greater width than as set forth above, including a width equal to the width of the center segments 106a-d, such as where the hinges are formed by pre-bending and heat setting the struts 55a-d at the desired hinge locations.

Figure 22:
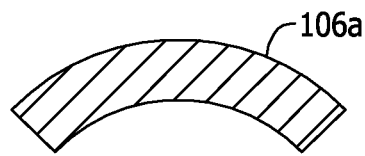
FIG. 22 is a transverse cross-section taken through a center segment of one strut of the electrode assembly of FIG. 3.
Figure 23:
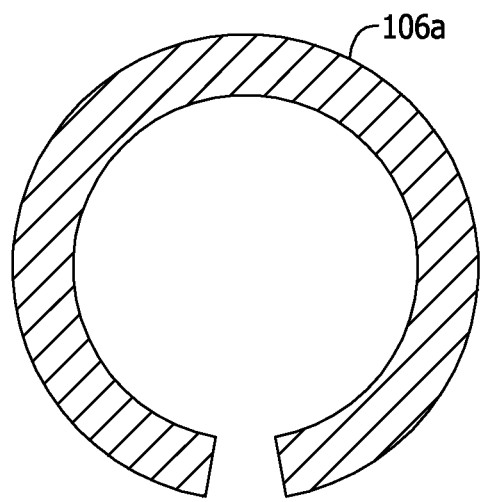
FIG. 23 is a transverse cross-section taken through a center segment of another embodiment of a strut suitable for use with the electrode assembly of FIG. 3.
Figure 24:
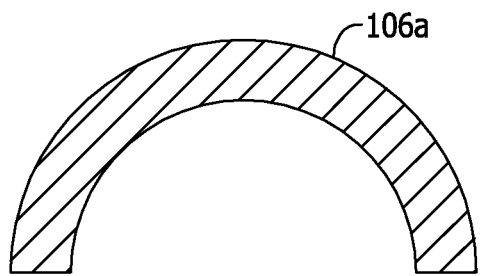
FIG. 24 is a transverse cross-section taken through a center segment of a third embodiment of a strut suitable for use with the electrode assembly of FIG. 3.
Figure 25:
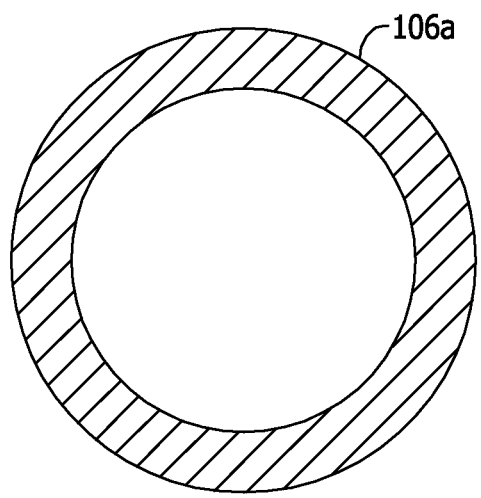
FIG. 25 is a transverse cross-section taken through a center segment of a fourth embodiment of a strut suitable for use with the electrode assembly of FIG. 3.
Figure 26:
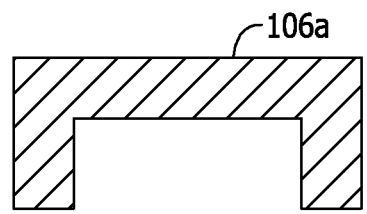
FIG. 26 is a transverse cross-section taken through a center segment of a fifth embodiment of a strut suitable for use with the electrode assembly of FIG. 3.
Figure 27:
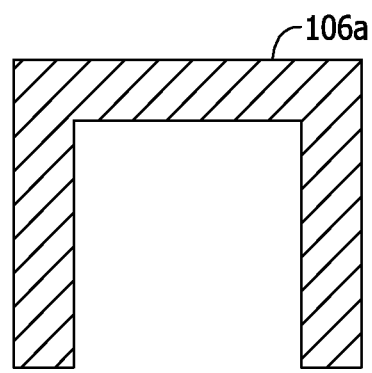
FIG. 27 is a transverse cross-section taken through a center segment of a sixth embodiment of a strut suitable for use with the electrode assembly of FIG. 3.

In other embodiments, at least the center segments 106a-d of the struts and optionally the proximal and/or distal ends 103a-d, 105a-d may be configured, e.g., in transverse cross-section, to have an increased stiffness (i.e., resistance to flexing or bending) relative to a strut that is generally flat in transverse cross-section. For example, as illustrated best in FIG. 22, at least the center segment 106a-d of each of the struts 55a-d of the electrode assembly 33 of FIG. 3 is generally arcuate or cambered in transverse cross-section along the length of the center segment. More particularly, as seen in FIG. 3, each of the struts 55a-d has a uniform arcuate transverse cross-section along its entire length, including the proximal and distal legs 103a-d, 105a-d of each strut.

However, it is understood that the center segment 106a-d of each strut 55a-d may be configured in transverse cross-section different from the proximal and distal legs 103a-d, 105a-d such that the center segment has a stiffness that is greater than the stiffness of each of the proximal leg and the distal leg. In such an embodiment (not shown), the difference in transverse cross-sectional configuration between the center segment 106a-d and the proximal leg 103a-d defines the one hinge 101a-d while the difference in transverse cross-sectional configuration between the center segment and the distal leg 105a-d defines the other hinge 102a-d. It is understood that the proximal and distal legs 103a-d, 105a-d may have the same transverse cross-sectional configuration as each other, or they may have different transverse cross-sectional configurations, within the scope of this disclosure.

Figure 28:
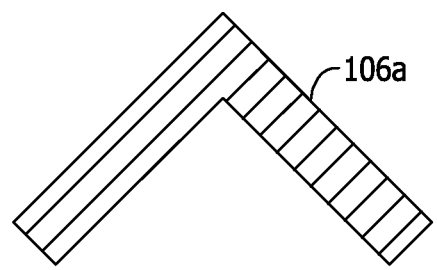
FIG. 28 is a transverse cross-section taken through a center segment of a seventh embodiment of a strut suitable for use with the electrode assembly of FIG. 3.
Figure 29:
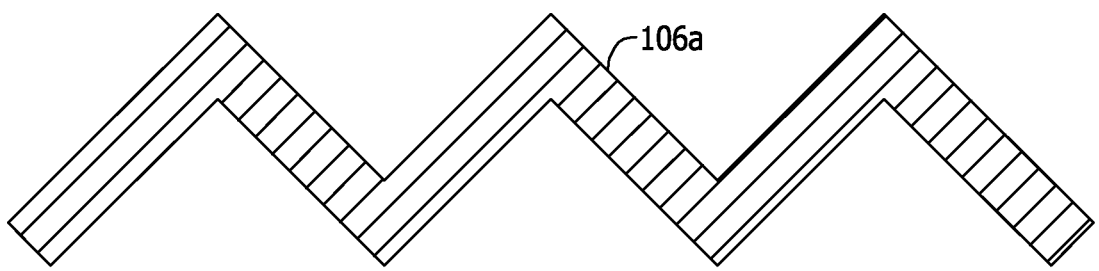
FIG. 29 is a transverse cross-section taken through a center segment of an eighth embodiment of a strut suitable for use with the electrode assembly of FIG. 3.

FIGS. 23-27 illustrate alternative transverse cross-section configurations of at least the center segment 106a-d (and optionally the proximal leg 103a-d and/or the distal leg 105a-d) of each strut 55a-d. For example, the transverse cross-section may be configured to be an almost closed circle (FIG. 23), semicircular (FIG. 24), circular (FIG. 25), generally C-shaped (FIG. 26), generally U-shaped (FIG. 27), generally V-shaped (FIG. 28), generally M-shaped or W-shaped (FIG. 29) or other suitable configuration.

Figure 30:
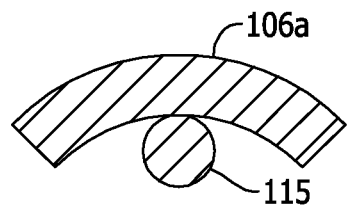
FIG. 30 is a transverse cross-section taken through a center segment of a ninth embodiment of a strut suitable for use with the electrode assembly of FIG. 3.
Figure 31:
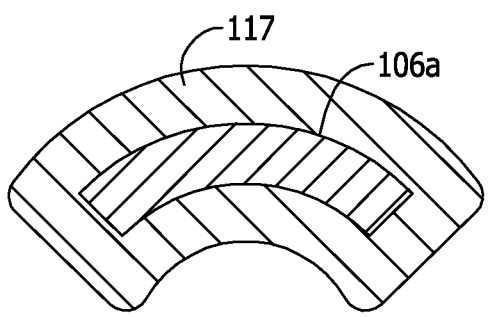
FIG. 31 is a transverse cross-section taken through a center segment of a tenth embodiment of a strut suitable for use with the electrode assembly of FIG. 3.

In other embodiments, the electrode assembly 33 may further include a stiffening element secured to or otherwise abutting at least the central segment 106a-d (and, optionally, the proximal leg 103a-d and/or the distal leg 105a-d) of each strut 55a-d to increase the stiffness thereof relative to a strut that lacks such a stiffening element. For example, in the illustrated embodiment of FIG. 30, the stiffening element comprises a relatively rigid wire 115 that may extend longitudinally along all or part of the length of at least the central segment 106a-d of each strut 55a-d in abutting relationship with the inner surface of the strut. The wire 115 adds rigidity to the central segment 106a-d of the strut 55a-d to thereby increase its stiffness. In the alternative embodiment of FIG. 31, the stiffening element comprises a relatively rigid sheath 117 that circumferentially surrounds at least the central segment 106a-d of each of the struts 55a-d along all or part of the length of the central segment. While in the illustrated embodiment the sheath 117 extends about the full circumference of the central segment 106a-d of each strut 55a-d, it is contemplated that in other embodiments the sheath may extend circumferentially about only a portion of the circumference of the central segment. It is also understood that the stiffening element may be any suitable stiffening element other than the wire of FIG. 30 or the sheath of FIG. 31. It is further understood that the stiffening element may further extend along all or part of the proximal leg 103a-d and/or the distal leg 105a-d of each strut 55a-d and remain within the scope of this disclosure.

Figure 32:
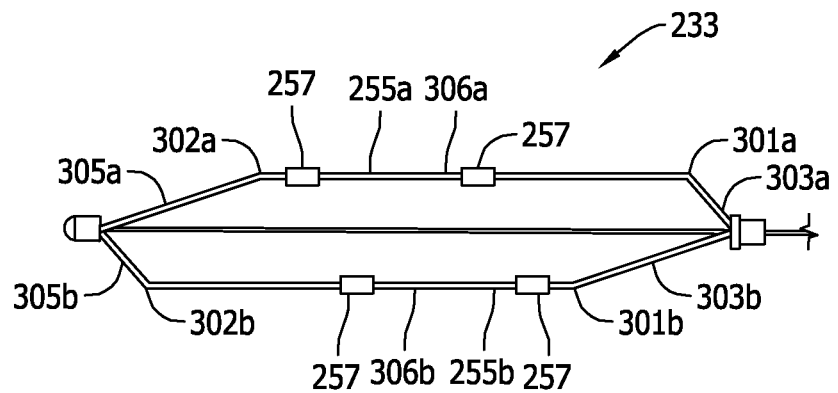
FIG. 32 is side elevation of a second embodiment of an electrode assembly, having a pair of struts, with the electrode assembly being illustrated in its collapsed configuration.
Figure 33:
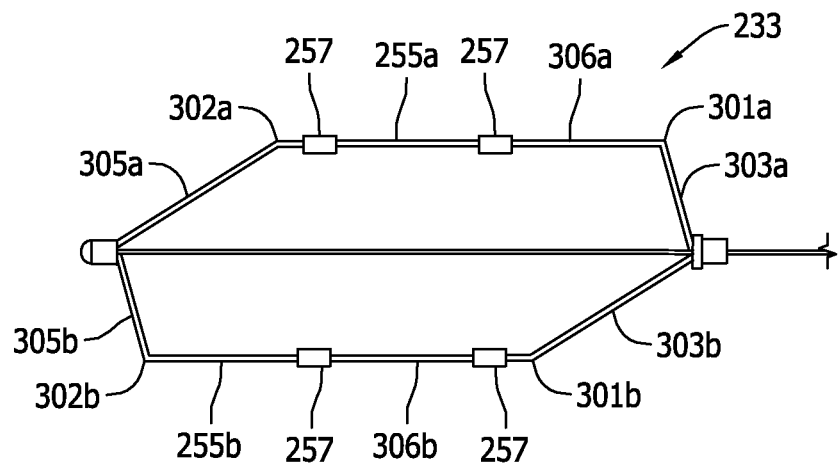
FIG. 33 is a side elevation of the electrode assembly of FIG. 32 illustrated in its expanded configuration.

With reference now to FIGS. 32 and 33, another embodiment of an electrode assembly 233 is illustrated as having a pair of struts 255a, b instead of the four struts 55a-d described in the previous embodiments. It is understood, however, that the electrode assembly 233 of this embodiment may have more than two struts 255a, b. As in the previous embodiments, each of the struts 255a, b of this embodiment has a proximal leg 303a, b, a distal leg 305a, b and a center segment 306a, b extending longitudinally between and interconnecting the proximal and distal legs. The one strut 255a has a hinge 301a intermediate and interconnecting the proximal leg 303a and the center segment 306a, and another hinge 302a intermediate and interconnecting the distal leg 305a and the center segment. The other strut 255b has a hinge 302a intermediate and interconnecting the proximal leg 303b and the center segment 306b, and another hinge 302b intermediate and interconnecting the distal leg 305b and the center segment 306b. The hinges 301a, b, 302 a, b may be configured in accordance with any of the hinge configurations illustrated and described herein.

Additionally, a pair of electrodes 257 is disposed on the center segment 306a, b of each of the struts 255a, b of this embodiment. In other embodiments there may be a single electrode 257 on each of the struts 255a, b, or there may be more than two electrodes on each of the struts. As best seen in FIG. 32, the electrodes 257 are disposed on the struts 255a, b at different longitudinal positions (i.e., different longitudinal distances from the proximal end of the electrode assembly 233) so that in the collapsed configuration of the electrode assembly the electrodes on one strut are at different longitudinal positions than the electrodes on the other strut. This arrangement facilitates circumferentially compressing the electrode assembly 233 down to a smaller cross-section beyond that of the preset collapsed configuration of FIG. 32 to facilitate positioning of the electrode assembly in a guide tube or lumen.

In this embodiment, for each strut 255a, b the length of the proximal leg 303a, b is different from the length of the distal leg 305a, b. For example, referring to the strut 255a, the proximal leg 303a thereof is shorter than the distal leg 305a of the strut. Additionally, the length of the proximal leg 303a of one strut 255a is different from the length of the proximal leg 303b of the other strut 255b. In the illustrated embodiment, for example, the proximal leg 303a of the one strut 255a is shorter than the proximal leg 303b of the other strut 255b. Also in the illustrated embodiment, the corresponding distal legs 305a, b of the struts 255a, b are of different lengths. In particular, the distal leg 305a of the one strut 255a (having the shorter proximal leg 303a) is longer than the distal leg 305b of the other strut 255b. Accordingly, the center segments 306a, b of the struts 255a, b are of a generally equal length. It is contemplated that in other embodiments the center segments 306a, b of the struts 255a, b may be of different lengths. In such embodiments the proximal legs 303a, b of the struts 255a, b may be of different lengths while the distal legs 305a, b are of a generally equal length, or the distal legs may be of different lengths while the proximal legs are of a generally equal length.

With the struts 255a, b configured in this manner, upon configuration of the electrode assembly 233 to its expanded configuration the center segments 306a, b become longitudinally offset from each other as illustrated in FIG. 33 due to the different lengths of the respective proximal and distal legs 303a, b, 305a, b of the struts. The electrodes 257 on the struts 255a, b, which are at different longitudinal positions in the collapsed configuration of the electrode assembly 233 (FIG. 32) suitably become positioned at substantially the same longitudinal position on each of the struts in the expanded configuration of the electrode assembly. In some ablation procedures it is advantageous to have the electrode(s) 257 on each strut 255a, b at generally the same longitudinal position.

Figure 34:
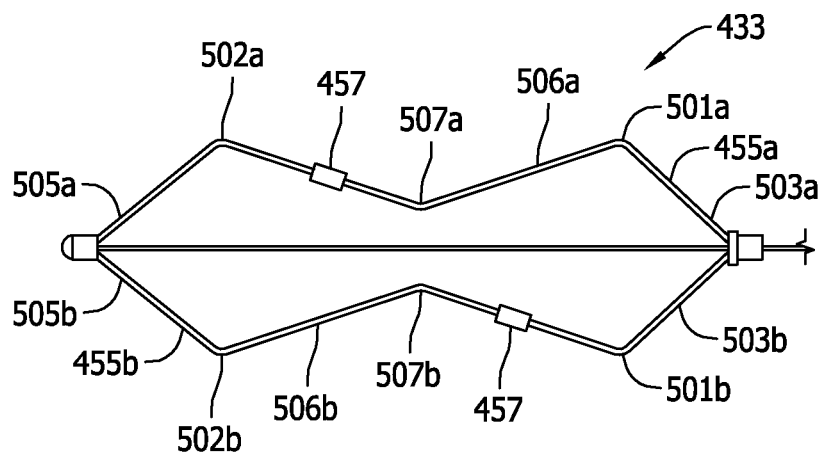
FIG. 34 is a side elevation of a third embodiment of an electrode assembly, having a pair of struts, with the electrode assembly being illustrated in its collapsed configuration.
Figure 35:
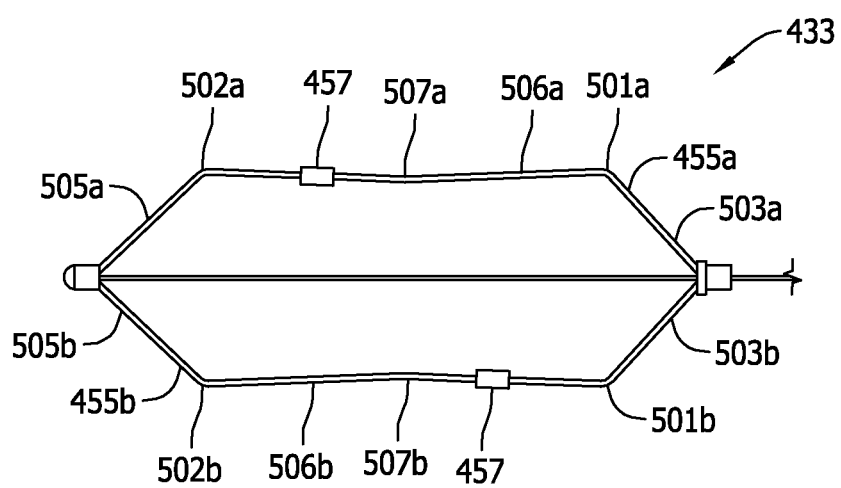
FIG. 35 is a side elevation of the electrode assembly of FIG. 34 illustrated in its expanded configuration.

FIGS. 34 and 35 illustrate another embodiment of an electrode assembly 433 having a pair of struts 455a, b. It is understood, however, that the electrode assembly 433 of this embodiment may have more than two struts 455a, b. As in the previous embodiments, each of the struts 455a, b of this embodiment has a proximal leg 503a, b, a distal leg 505a, b and a center segment 506a, b extending longitudinally between and interconnecting the proximal and distal legs. Each strut 455a, b also has a first hinge 501a, b intermediate and interconnecting the proximal leg 503a, b and the center segment 506a, b, and a second hinge 502a, b intermediate the distal leg 505a, b and the center segment. The hinges 501a, b, 502a, b may be configured in accordance with any of the hinge configurations illustrated and described herein.

In this embodiment, the center segment 506a, b of each strut 455a, b is configured to be generally concave as it extends lengthwise between the proximal and distal legs 503a, b, 505a, b of the electrode assembly 433. The concave configuration of the center segment 506a, b may be formed by including a hinge 507a, b (having any of the configurations illustrated and described herein) intermediate the longitudinal ends of the center segment 506a, b, or by arching, or bowing the center segment transversely inward and heat setting the center segment in such an arched or bowed configuration to define the collapsed configuration of the electrode assembly 433 as illustrated in FIG. 34.

Upon configuration of the electrode assembly 433 to its expanded configuration, as illustrated in FIG. 35, the proximal and distal legs 503a, b, 505a, b of each strut 455a, b are urged generally longitudinally outward while the center segment 506a, b is urged to un-bow to the extent that the center segment is less arched or bowed, or is more suitably only slightly arched or bowed, and is even more suitably generally straight, or flat in the expanded configuration of the electrode assembly. While in the illustrated embodiment the hinges 501a, b, 502a, b and 507a, b are illustrated as being a relatively sharp bend, it is understood that in other embodiments one or more of the hinges may be formed as a more gradual or rounded configuration and remain with the scope of this disclosure. The corresponding electrodes 457 on each strut 455a, b are suitably at different longitudinal positions, for reasons discussed previously herein, and in the illustrated embodiment they are each positioned on the respective center segment 506a, b of the strut.

Figure 36:
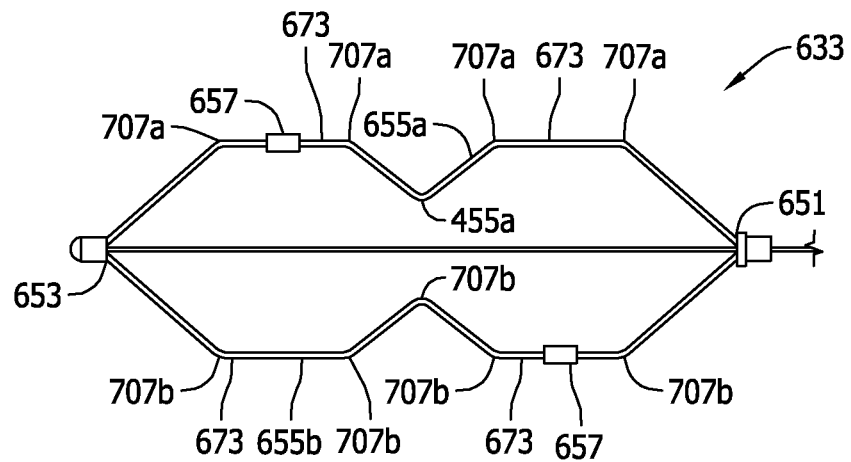
FIG. 36 is a side elevation of a fourth embodiment of an electrode assembly, having a pair of struts, with the electrode assembly being illustrated in its collapsed configuration.
Figure 37:
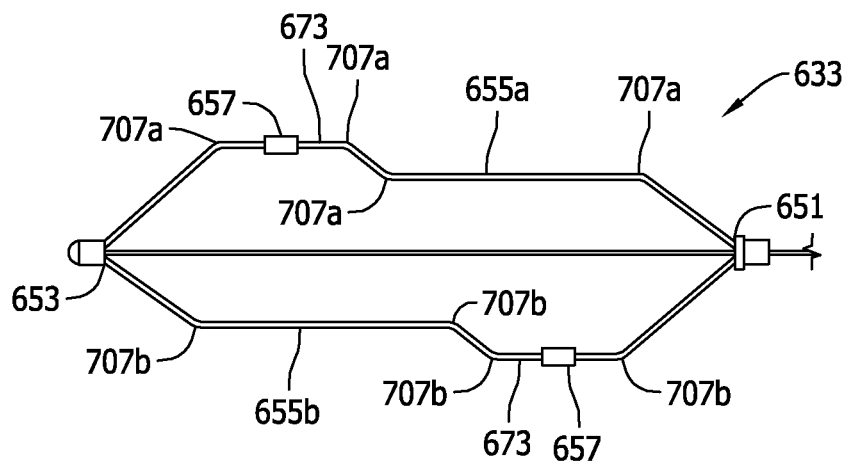
FIG. 37 is a side elevation of a fifth embodiment of an electrode assembly, having a pair of struts, with the electrode assembly being illustrated in its collapsed configuration.
Figure 38:
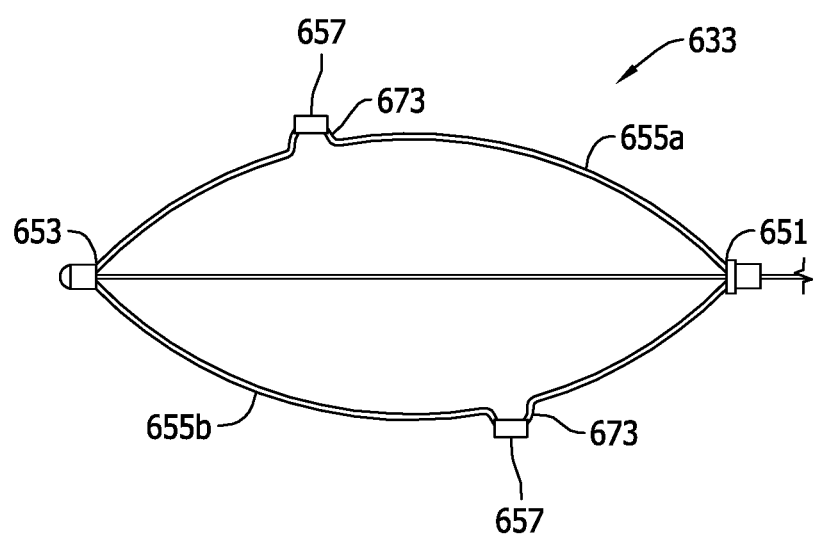
FIG. 38 is a side elevation of a sixth embodiment of an electrode assembly, having a pair of struts, with the electrode assembly being illustrated in its collapsed configuration.

FIGS. 36, 37 and 38 each illustrate further alternative embodiments of an electrode assembly 633, each having a pair of struts 655a, b. It is understood, however, that the electrode assemblies 633 of these embodiment may have more than two struts. Each of the struts 655a, b has a riser element 673 intermediate the proximal and distal ends 651, 653 of the electrode assembly 633 to facilitate a greater transversely outward point of contact of the electrodes against the arterial wall upon configuring the electrode assembly in its expanded configuration. In the illustrated embodiment of FIG. 36, for example, each strut 655 a, b has a pair of riser elements 673—with each riser element comprising a generally trapezoidal configuration formed in the strut. Each riser element may be formed in the respective strut using one or more hinges 707a, b. In this embodiment, one hinge 707a, b is common to both of the riser elements 673 on each strut 655a, b. It is understood, however, that the riser elements 673 on each strut 655a, b may be discrete from each other, e.g., without sharing a common hinge 707a, b. The hinges 707 a, b may each be configured in accordance with any of the hinge configurations described previously herein. Upon configuration of the electrode assembly 633 to its expanded configuration (not shown), the riser element 673 of each strut 655a, b defines the transversely outermost extent of the respective strut. The electrodes 657 of the electrode assembly 633 are each disposed on a respective one of the riser elements 673 to facilitate apposition of the electrodes against the arterial wall.

In the embodiment illustrated in FIG. 37, the struts 655a, b of the electrode assembly 633 each include a single riser element 673 comprised of a generally trapezoidal configuration formed in the strut. As in the previous embodiment, each riser element 673 is suitably formed in the respective strut 655 a, b using suitable hinges 707a, b. In the embodiment of FIG. 38, each of the struts 655a, b is generally arcuate in the collapsed configuration of the electrode assembly 633. Each of the riser elements 673 comprises a generally rounded bump formed and preset in the strut 655 a, b intermediate the proximal and distal ends of the electrode assembly 633. It is understood that the bump 673 may be larger or smaller than as illustrated in FIG. 38 without departing from the scope of this disclosure. It is also understood that the riser elements 673 may be formed in the struts 655a, b of the electrode assembly 633 in any other suitable manner and/or configuration without departing from the scope of this disclosure.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. An electrode assembly for an electrode catheter system, the electrode assembly having a longitudinal axis, a proximal end and a distal end, the electrode assembly comprising:
    first and second struts each extending from the proximal end to the distal end of the electrode assembly and having a corresponding electrode disposed thereon intermediate said proximal and distal ends of the electrode assembly, wherein the electrode assembly is configurable between a collapsed configuration and an expanded configuration, the electrodes being transversely spaced from the longitudinal axis of the electrode assembly a greater distance in the expanded configuration than in the collapsed configuration, in the collapsed configuration the electrode on the first strut being at a first longitudinal position intermediate the proximal and distal ends of the electrode assembly and the electrode on the second strut being at a second longitudinal position intermediate the proximal and distal ends of the electrode assembly and different from the first longitudinal position of the electrode on the first strut, in the expanded configuration the first longitudinal position of the electrode on the first strut being substantially equal to the second longitudinal position of the electrode on the second strut.

2. The electrode assembly of claim 1 wherein each of the first and second struts comprises a longitudinally extending proximal leg, a longitudinally extending distal leg, and a center segment extending between and interconnecting the proximal leg and the distal leg, the corresponding electrodes being disposed on the center segment of each respective one of the first and second struts, the proximal leg of the first strut having a first length and the proximal leg of the second strut having a second length different from the first length of the proximal leg of the first strut.

3. The electrode assembly of claim 2 wherein the center segment of the first strut has a first length and the center segment of the second strut has a second length substantially equal to the first length of the center segment of the first strut.

4. The electrode assembly of claim 2 wherein the distal leg of the first strut has a first length and the distal leg of the second strut has a second length different from the first length of the distal leg of the first strut.

5. The electrode assembly of claim 2 wherein each strut further comprises a first hinge interconnecting the proximal leg and the center segment, and a second hinge interconnecting the distal leg and the center segment.

6. The electrode assembly of claim 2 wherein the center segment of each strut has a cross-section configuration, at least one of the proximal leg and the distal leg of each strut having a cross-section configuration that is different from the cross-section configuration of the center segment.

7. The electrode assembly of claim 6 wherein the cross-section configuration of the center segment of each strut is selected from the group consisting of: cambered, semicircular, circular, almost closed semicircular, C-shaped, U-shaped, V-shaped, W-shaped, and M-shaped.

8. The electrode assembly of claim 2 further comprising, for each strut, a respective stiffening element at least one of on and abutting at least the center segment of the strut to increase the stiffness thereof.

9. An electrode assembly for an electrode catheter system, the electrode assembly having a longitudinal axis, a proximal end and a distal end, the electrode assembly comprising: a plurality of struts each extending from a first common location at the proximal end of the electrode assembly to a second common location at the distal end of the electrode assembly, each strut including an integral riser element intermediate the proximal end and the distal end of the electrode assembly, wherein each riser element is located a respective longitudinal distance from the first common location at the proximal end of the electrode assembly, the riser element of one strut being hingedly coupled to a proximal portion of the one strut at a first longitudinal distance and extending linearly along an axis parallel to the longitudinal axis to a distal portion of the one strut, the riser element of a transversely opposite strut being hingedly coupled to a proximal portion of the transversely opposite strut at a second longitudinal distance that is different from the first longitudinal distance and extending linearly along an axis parallel to the longitudinal axis to a distal portion of the transversely opposite strut, the electrode assembly being configurable between a collapsed configuration and an expanded configuration, in the expanded configuration the riser element of each strut extending transversely outward from the proximal portion of the respective strut, with respect to the longitudinal axis of the electrode assembly, a greater distance than any other point of the respective strut, each strut further having an electrode disposed on the respective riser element at a location on the respective riser element that is at a greatest transverse distance from the longitudinal axis.

10. The electrode assembly of claim 9 wherein the electrode assembly has a length from its proximal end to its distal end, the length of the electrode assembly decreasing upon configuration of the electrode assembly from its collapsed configuration to its expanded configuration.

11. The electrode assembly of claim 9 wherein the struts are formed integrally with each other.

12. The electrode assembly of claim 9 in combination with the catheter system, the catheter system comprising a handle, an elongate shaft extending from the handle, the electrode assembly, and an actuator associated with the handle and operatively connected to the electrode assembly for selectively configuring the electrode assembly from its collapsed configuration to its expanded configuration.

13. An electrode assembly for an electrode catheter system, the electrode assembly having a longitudinal axis, a proximal end and a distal end, the electrode assembly comprising:

a plurality of struts each extending from the proximal end to the distal end of the electrode assembly and each having a corresponding electrode thereon located a respective longitudinal distance from the proximal end of the electrode assembly, wherein the electrode assembly is configurable between a collapsed configuration and an expanded configuration, the electrodes being transversely spaced from the longitudinal axis of the electrode assembly a greater distance in the expanded configuration than in the collapsed configuration, in the collapsed configuration each of the struts having a generally concave segment extending lengthwise along the strut intermediate the proximal and distal ends of the electrode assembly, the concave segment including a first portion hingedly coupled to a proximal portion of the respective strut and a second portion hingedly coupled to the first portion and to a distal portion of the respective strut, the electrode of the respective strut being located on the first portion of the generally concave segment at a first longitudinal distance, and the electrode of at least one other strut being located on the second portion of the generally concave segment at a second longitudinal distance that is different from the first longitudinal distance.

14. The electrode assembly of claim 13 wherein in the expanded configuration said segment of the strut is less concave than in the collapsed configuration of the electrode assembly.

15. The electrode assembly of claim 13 wherein in the expanded configuration said segment of the strut is generally flat along its length.

* * * * *